(12) United States Patent
Hansmann et al.

(10) Patent No.: US 10,648,963 B2
(45) Date of Patent: May 12, 2020

(54) TESTING DEVICE FOR TESTING A GAS GUIDE ELEMENT

(71) Applicant: Drägerwerk AG & Co. KGaA, Lübeck (DE)

(72) Inventors: Hans-Ullrich Hansmann, Barnitz (DE); Henning Gerder, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 0 days.

(21) Appl. No.: 15/817,768

(22) Filed: Nov. 20, 2017

(65) Prior Publication Data

US 2018/0143170 A1    May 24, 2018

(30) Foreign Application Priority Data

Nov. 23, 2016  (DE) .......................... 10 2016 013 959

(51) Int. Cl.
  *G01N 33/00*    (2006.01)
(52) U.S. Cl.
  CPC ....... *G01N 33/007* (2013.01); *G01N 33/0008* (2013.01)
(58) Field of Classification Search
  CPC .......... G01N 33/07; G01N 2033/0072; G01N 33/0006; G01N 33/0008; G01N 33/007; E21B 47/1025; G08B 21/20; G01M 3/18; G01M 3/182; G01M 3/183; G01M 3/04; G01M 3/08; G01M 3/083; G01M 3/085
  USPC .......... 73/1.06, 1.01, 37, 40, 40.5 R, 40.5 A, 73/49.1; 340/605
  See application file for complete search history.

(56) References Cited

U.S. PATENT DOCUMENTS

| | | | | |
|---|---|---|---|---|
| 2,353,287 | A | * | 7/1944 | Benesh ............... G01M 3/2807 405/54 |
| 6,119,710 | A | | 9/2000 | Brown |
| 6,237,392 | B1 | | 5/2001 | Yu et al. |
| 7,406,854 | B2 | | 8/2008 | Lange et al. |
| 7,645,367 | B2 | | 1/2010 | Tschuncky et al. |
| 2018/0143171 | A1 | * | 5/2018 | Hansmann .......... G01M 3/2807 |

FOREIGN PATENT DOCUMENTS

| | | |
|---|---|---|
| CN | 1350668 A | 5/2002 |
| CN | 101375158 A | 2/2009 |
| CN | 105606320 A | 5/2016 |
| DE | 10 2005 045 272 B4 | 10/2007 |

(Continued)

*Primary Examiner* — Robert R Raevis
(74) *Attorney, Agent, or Firm* — McGlew and Tuttle, P.C.

(57) ABSTRACT

A testing device (1) is configured for testing a gas guide element (3). A control unit (70) carries out a sequence of steps with two operating states. A test gas (91) is delivered by a pumping device (7) through the gas guide element (3) to a remotely located measuring location (80) and is subsequently delivered from the remotely located measuring location (80) to the gas sensor system (5). Measured values (77) are detected and analyzed during the delivery from the remotely located measuring location (80) to the gas sensor system (5) by a sensor (6, 90), which indicates a state of flow in the gas guide element (3) or an operating state of the pumping device (7). Changes occurring in the measured values (77) during the delivery from the remotely located measuring location (80) to the gas sensor system (5) indicate the operational capability of the gas guide element (3).

17 Claims, 7 Drawing Sheets

(56) References Cited

FOREIGN PATENT DOCUMENTS

| | | |
|---|---|---|
| DE | 20 2006 020 536 U1 | 11/2008 |
| DE | 10 2013 008 425 B3 | 5/2014 |
| DE | 10 2014 221 499 A1 | 4/2016 |
| DE | 10 2015 003 745 A1 | 9/2016 |
| DE | 10 2015 015 152 A1 | 6/2017 |
| TW | 431600 U | 4/2001 |
| WO | 99/17110 A1 | 4/1999 |
| WO | 2007/087 403 A2 | 8/2007 |

\* cited by examiner

TESTING DEVICE FOR TESTING A GAS GUIDE ELEMENT

CROSS REFERENCE TO RELATED APPLICATIONS

This application claims the benefit of priority under 35 U.S.C. § 119 of German Application 10 2016 013 959.5, filed Nov. 23, 2016, the entire contents of which are incorporated herein by reference.

FIELD OF THE INVENTION

The present invention pertains to a testing device for testing a gas guide element in a gas-measuring system and pertains to a testing of the gas guide element by means of a pumping device.

BACKGROUND OF THE INVENTION

Gas-measuring systems are used for industrial gas measurement and protect persons who are located in areas or rooms from hazards to health and life. Industrial gas measurement is important in an industrial environment, such as in the petrochemical industry, refineries, chemical industry, for monitoring explosive or toxic gases or vapors. Both mobile and stationary devices are used here. Combinations of mobile or stationary devices are also used to make it possible to perform gas concentrations or gas analyses in storage tanks, boreholes or silos.

Thus, a combination of a mobile gas-measuring device and a pump is known from DE 10 2005 045 272 B4. It is thus possible to also use mobile gas-measuring devices for measuring gas concentrations in a main shaft, tank or in a borehole. Gas can be delivered to the gas-measuring device by means of the pump and an element for gas delivery, preferably a hose line. The pump is controlled in terms of the start of delivery, flow rate, end of delivery and other operating characteristics of the pump by the mobile gas-measuring device or the control thereof.

A possibility for testing a sensor system and a hose line of a gas-measuring system, which can be carried out essentially only once, is known from DE 10 2015 003 745 from the area of mobile gas measuring technology. A quantity of gas sample positioned at the end of the hose is introduced into the hose line by means of a remote release and fed to the gas-measuring system, so that testing of the sensor system and of the hose line is made possible.

A gas sensor with an adapter is known from U.S. Pat. No. 7,406,854 B2. The adapter is configured to form a port of a hose line. It is possible via this hose line to feed gas from a remotely located measuring location to the gas sensor. This delivery of gas may be carried out, for example, by means of a feed pump.

Gas-measuring systems comprising a gas sensor and a gas generator are known from WO 1999/17110 A1 as well as U.S. Pat. No. 7,645,367. Such combinations of gas generators and gas sensors make it possible to test the measuring properties of the gas sensors, especially to determine whether the gas sensor responds sensitively to the admission of a measured gas concentration generated by the gas generator.

A device for testing a gas sensor is known, for example, from DE 20 2006 020 536 U1. A gas generator, which is suitable for generating ethane, is described there. The gas generator is intended for testing the gas sensor and is configured to dispense a certain quantity of a gas to/into the gas sensor, and a change or response of the output signal of the gas sensor, which change or response is based on this, is an indication that the gas sensor is able to function.

Recommendations have been issued by the Occupational Safety and Health Administration (OSHA) of the U.S.A. concerning function tests with so-called "bump tests," wherein a regular testing of gas sensors can be carried out by means of suitable adapters and a suitable gas.

U.S. Pat. No. 7,406,854 B2 describes an adapter for testing or calibrating an electrochemical gas sensor. The adapter can preferably be arranged on the gas sensor with a Velcro fastener and can be removed again from same after the testing or calibration has been carried out.

The state of the art cited does not show any solutions for the repeated or regular testing of the operational capability in gas-measuring systems with gas feed lines or hose lines that are provided for feeding gas from a remotely located measuring location to a gas sensor system and are arranged in the gas-measuring systems. Ensuring the functional capability of the feed lines or hose lines as well as the connection elements thereof is just as essential for a reliable operation of the gas-measuring systems as the operational capability of the gas sensor system itself. Leaks in the gas feed lines, hose lines or connection elements (plugs, couplings, sockets, bonded joints, soldered connections, welded connections) bring about changes in the gas concentrations on the way from the measuring location to the gas sensor system, which may cause as a consequence an incorrect measurement with consequential incorrect assessments, measured value outputs and alarms concerning current situations at the measuring location. Leaks result, for example, from holes, cracks, kinks or porous partial sections in hose lines as well as from holes, for example, those caused by material fatigue in systems and corresponding screwed, plug-type or soldered connections or line couplings.

A regular, repeatable testing of the operational capability of the gas feed lines, hose lines and connection elements, which can be combined under a generic term of gas guide elements, is therefore of great significance.

Especially in the case of already existing plants or installations of gas-measuring systems with a plurality of gas sensors, there is need for testing the operational capability of the plant during the operation on a regular basis. In particular, there is need, in addition to the testing of the gas sensors, for also testing lines and gas feed lines. For installation situations in which the quantities of gas to be analyzed are fed to the gas sensors from locations located at a distance from the site of installation of the gas sensors by means of gas feed lines, it is advantageous to test the operational readiness and/or operational capability of the gas feed lines as well.

SUMMARY OF THE INVENTION

With the knowledge of the above-described known state of the art and analysis of the drawbacks of the known state of the art, an object of the present invention is therefore to provide a device that makes it possible a test of operational capabilities of gas feed lines in a gas-measuring system.

The testing device according to the present invention for testing a gas guide element in a gas-measuring system that has the gas guide element, a pumping device with a pump configured suitably for delivering a gas, a state of flow sensor, which indicates a state of flow in the gas guide element or an operating state of the pumping device, a gas sensor system, which is configured to detect concentrations of gases. The testing device comprises a test gas source, and a control unit with connections to the pumping device, the state of flow sensor and the gas sensor system.

The terms measured gas, test gas, scavenging gas and resetting gas used within the framework of this patent application will be explained in more detail at the beginning.

A measured gas is defined as a gas or gas mixture that is such that the gas sensor system is sensitive to changes in a gas concentration of this measured gas and responds with changes in the gas concentration measured value to changes in a gas concentration of this measured gas.

A scavenging gas or a resetting gas is defined as a gas that is such that the gas sensor system is not sensitive to changes in the gas concentration of this gas or gas mixture and it does not respond to changes in the gas concentration of this scavenging gas or resetting gas with changes in the gas concentration measured value.

A test gas is defined as a gas or a gas mixture whose density and/or whose viscosity are different from the density and/or viscosity of an ambient gas mixture, preferably also from the density and/or viscosity of the resetting gas and from the density and/or viscosity of the measured gas and is preferably such that it is irrelevant whether the gas sensor system is sensitive or insensitive to changes in the gas concentration of the test gas. Advantageous is in this connection a test gas to the presence or concentration change of which the gas sensor system is not sensitive to produce a response in the sensor system during the testing of the operational capability of the gas guide element. The ambient air mixture has a usual composition now with essential percentages of oxygen (~21%), nitrogen (~78%), water vapor, carbon dioxide and noble gases.

The sensor, which indicates the state of flow in the gas guide element or an operating state of the pumping device, is preferably configured as a pressure sensor or as a flow sensor and is arranged in the testing device in or close to the pumping device at the gas guide element.

The sensor, which indicates the state of flow in the gas guide element or an operating state of the pumping device, may also be configured as a speed of rotation sensor for detecting a speed of rotation of the pump arranged in the pumping device.

The pressure sensor is configured to detect a measured value, which indicates a pressure in the gas guide element, and to make it available to the control unit. The pressure sensor is arranged at the pumping device or at the gas guide element as close to the pumping device as possible such that the pressure sensor can detect a pressure occurring in the gas guide element. The pressure sensor is preferably configured as a pressure sensor for detecting an absolute pressure level in the gas guide element or as a pressure sensor for measuring a pressure difference of the gas relative to the ambient pressure in the gas guide element.

The flow sensor is designed to detect a flow rate flowing in the gas guide element or a flow velocity of the quantity of gas of the test gas or measured gas. The flow sensor makes the detected flow rate available to the control unit as a value of the detected flow rate. The flow sensor is preferably configured here as a differential pressure sensor ($\Delta P$ sensor), which detects a pressure difference over a diaphragm arranged in the gas guide element (flow resistance).

The pressure sensor is configured as an absolute pressure sensor for detecting the absolute pressure level of a gas or gas mixture in the gas guide element. The pressure sensor is configured, as an alternative, as a relative pressure sensor for detecting a pressure difference of the gas or gas mixture in the gas guide element relative to the pressure of the ambient air mixture. The pressure sensor and/or the flow sensor ($\Delta P$ sensor) are sensitive during the measurement to differences in the density and/or the viscosity of the test gas compared to the density and/or the viscosity of the ambient air and preferably also relative to the density and/or the viscosity of the measured gas and respond to changes in the gas composition of the gas mixture with changes in the density and/or viscosity of the gas mixture, which changes depend on changes in the gas composition, and with changes in the measured value.

The control unit is configured to control, i.e., set, control or regulate the pump in the pumping device in terms of the delivery rate and/or the flow rate and/or the delivery pressure on the basis of the measured values of the pressure and/or of the measured values of the flow rate.

It is essential for the present invention that the sensor, which indicates the state of flow in the gas guide element or an operating state of the pumping device, be present as a sensory element for setting the pumping device, and it is, in addition, used to test the gas guide element.

The sensor, which indicates the state of flow in the gas guide element or an operating state of the pumping device, is used during the testing to also detect changes in the density and/or viscosity of the test gas by measurements.

The pumping device with a pump, which is arranged in the pumping device or is associated with the pumping device and which carries out the feed of the measured gas from the remotely located measuring location to the gas sensor system in cooperation with the gas guide element, is likewise used for testing the operational capability of the gas guide element.

Two essential components, namely, the sensor, which indicates the state of flow in the gas guide element or an operating state of the pumping device (pressure sensor, flow sensor, speed of rotation sensor), and the pumping device with the pump are thus already present as essential components in the gas-measuring system. The object of the present invention, namely, the testing of the operational capability of the gas guide element in the gas-measuring system, can be accomplished in the gas-measuring system, whose basic functions are known, with a variation of the pumping device and with an addition to the control of the pumping device with the features of the present invention and by including the tests.

The components of the gas-measuring system, the functions thereof and the interaction thereof for testing the gas guide element in the gas-measuring system will be explained in more detail below.

The gas guide element is used for the gas-carrying connection of the gas sensor system to the measuring location, which is located remotely in space or is arranged at a distance from this gas sensor system. Such a measuring location located remotely in space or arranged at a distance is, for example, a measuring location in underground or above-ground storage tanks or silos, main shafts, inspection shafts, boreholes and similar or comparable measuring locations.

The gas sensor system comprises at least one gas sensor in a gas-measuring system and is intended to cyclically or continuously detect a measured gas or a plurality of measured gases fed by means of the gas guide element by measurement cyclically or continuously and to analyze it qualitatively as well as quantitatively and to make it available to the control unit as gas concentration measured values in the gas-measuring system.

The gas-measuring system is used here to detect and determine gas concentrations as well as to monitor distinctive threshold values derived from the gas concentrations, for example, the so-called "lower explosive limit" (LEL) or toxic limit values, such as the so-called threshold limit value (TLV).

The measuring environment may be formed here directly at or close to the side of the gas sensor system for some of the gas sensors.

The measuring environment for the gas sensor system is also formed by the remotely located measuring location, from which measured gas is fed by means of the gas guide element and the pumping device to the gas sensor system for detection for the purpose of a qualitative analysis (gas mixture composition) and/or quantitative gas analysis (gas concentration).

The gas guide element may be configured as a flexible hose line or a semiflexible or rigid pipeline system as well as a combination of hose line elements and pipeline elements, so that one-piece as well as multi-piece or multi-part connections may be formed between the remotely located measuring location and the gas-measuring device.

The gas guide element or an array of gas guide elements is arranged between the remotely located measuring location, the pumping device with the sensor (pressure sensor, flow sensor, speed of rotation sensor), which indicates the state of flow in the gas guide element or an operating state of the pumping device, and the gas sensor system.

The gas guide element, the sensor (pressure sensor, flow sensor), which indicates the state of flow in the gas guide element or an operating state of the pumping device, the gas sensor system and the pumping device are connected to one another fluidically and are configured for a cooperation such that a quantity of gas can be fed to the gas sensor system and to the sensor (pressure sensor, flow sensor, speed of rotation sensor), which indicates the state of flow in the gas guide element or an operating state of the pumping device, from the measuring location located remotely from the gas sensor system, and a quantity of gas can be fed by the pumping device to the remotely located measuring location.

The test gas source is arranged at the pumping device such that the gas guide element, the gas sensor system and the pumping device are connected fluidically such that test gas can be fed as a quantity of gas from the test gas source to the remotely located measuring location. The test gas source may also be configured as a part of the pumping device, and the pumping device may likewise also be configured as a part of the test gas source.

For carrying out the present invention, the test gas being stored in the test gas source is a gas that has a significant difference in its density and/or viscosity compared to ambient air and compared to a gas mixture from ambient air and the measured gas at the usual concentration. The significant difference in the density and/or viscosity of the test gas from the density of the ambient air makes it possible to test the gas guide element for its operational capability.

Table 1 below shows an overview of the different gases and their density $\rho$.

TABLE 1

| Gas | Chemical formula/ Empirical formula | Density $\rho$ [kg/m$^2$] at 0° C., 1,013 hPa |
|---|---|---|
| Carbon dioxide | CO$_2$ | 1.98 |
| Helium | He | 0.18 |
| Methane | CH$_4$ | 0.656 |
| Propane | C$_3$H$_8$ | 2.01 |
| Xenon | Xe | 5.89 |
| Neon | Ne | 0.9 |

TABLE 1-continued

| Gas | Chemical formula/ Empirical formula | Density $\rho$ [kg/m$^2$] at 0° C., 1,013 hPa |
|---|---|---|
| Dinitrogen monoxide | N$_2$O (laughing gas) | 1.98 |
| Ambient air | O$_2$~21%, N$_2$~78%, H$_2$O, CO$_2$, noble gases | 1.29 |

Table 2 below shows an overview of different gases and their dynamic viscosities $\eta$.

TABLE 2

| Gas | Chemical formula/ Empirical formula | Dyn. viscosity $\eta$ [µNs/m$^2$] at 0° C., 1,013 hPa |
|---|---|---|
| Carbon dioxide | CO$_2$ | 14.6 |
| Helium | He | 19.7 |
| Methane | CH$_4$ | 11.2 |
| Propane | C$_3$H$_8$ | 7.9 |
| Xenon | Xe | 22.3 |
| Neon | Ne | 31.1 |
| Dinitrogen monoxide | N$_2$O (laughing gas) | 14.3 |
| Ambient air | O$_2$~21%, N$_2$~78%, H$_2$O, CO$_2$, noble gases | 17.1 |

If it is assumed for an application that conditions that can be characterized essentially by the presence of ambient air prevail at the remotely located measuring location in the absence of the measured gas, test gases that show the greatest possible different in density and/or dynamic viscosity from ambient air are suitable.

It can therefore be determined from Tables 1 and 2 above that helium as well as xenon have a significant difference in density from that of ambient air and are thus well suited for use as test gases.

It can therefore be determined from Tables 1 and 2 above that propane as well as xenon have a significant different in viscosity from ambient air and are thus well suited for use as test gases.

The quantity of gas as a test gas present in the gas guide element has a direct effect on the measured values detected by means of the pressure sensor and/or flow sensor arranged in or at the pumping device or in or at the gas guide element.

The effect of a significant difference in the densities of two different quantities of gas delivered by the pump is that in case of operating the pump at a constant speed of rotation or constant flow rate $\dot{V}$, the measured value that can be detected with the pressure sensor at the pump is proportional to the difference in the densities of the two quantities of gas.

The effect of a significant difference in the dynamic viscosities of two different quantities of gas delivered by the pump is that in case of operating a pump arranged in the pumping device at a detected or estimated flow rate $\dot{V}$, the ratio of the measured value that can be detected with the pressure sensor at the pump to the flow rate being delivered is proportional to the difference in the viscosities of the two quantities of gas.

It is thus possible by means of the sensor (pressure sensor, flow sensor, speed of rotation sensor), which indicates the state of flow in the gas guide element or an operating state of the pumping device, especially by means of the pressure sensor, depending on the configuration of the pumping device with pressure sensors and preferably also with flow sensors, to test the operational capability of the gas guide element. Depending on this configuration and the implemented variant of the control of the delivery of the quantities of gas by means of the control/regulation, e.g., by means of a speed of rotation/pressure characteristic, a characteristic of the delivery pressure and electric current or power consumption, a characteristic of the speed of rotation and flow rate, an adjustment of the speed of rotation of the pump on the basis of a sensor for detecting flow velocities or flow rates $\dot{V}$, a gas with a significantly lower or higher density compared to the ambient air or a test gas with a significantly lower or higher viscosity compared to the ambient air will be used as a test gas.

A known or detected system variable, which is present in the pumping device or in the control unit for the operation of the pump, is used according to the present invention to test the operational capability of the gas guide element. The system variable represents a current density and/or dynamic viscosity of a gas or gas mixture present in the gas guide element.

Measured values detected by means of the sensor (pressure sensor, flow sensor, speed of rotation sensor), which indicates the state of flow in the gas guide element or an operating state of the pumping device, represent a first possible configuration of the system variable, which represents differences in the density and/or in the dynamic viscosity of the test gas. The sensor (pressure sensor, flow sensor, speed of rotation sensor), which indicates the state of flow in the gas guide element or an operating state of the pumping device, consequently also makes it possible to test the operational capability of the gas guide element according to the present invention.

Another possible configuration of the system variable, which represents differences in the density and/or in the dynamic viscosity of the test gas, is given by parameters that indicate operating states of the pump. Depending on the configuration of the control with controlling or regulating the pump, a parameter is obtained as a system variable, which represents a current density and/or dynamic viscosity of the gas or gas mixture in the gas guide element in the interaction between the electrical output of the pump, electric current consumption, electric actuating signal, e.g., by means of pulse width modulation (PWM), flow rate and pressure.

The aspect that the test gas being used should not damage the gas guide element, the pumping device, the gas sensor system nor cause environmental or health hazards at the concentration used should also play a role when selecting the suitable test gas in addition to the task of the measurement of the gas-measuring device with the measured gases to be analyzed and with the suitable configuration of the pumping device with the sensor system and control or regulation and the fact that the measurement effect should be able to be detected by the pressure sensor and/or by the flow sensor with sufficient signal quality based on a difference in densities or a difference in viscosities.

The control unit is configured to receive measured values detected and provided by the gas sensor system and the pressure sensor and/or the flow sensor. The control unit is further configured to store the measured values detected and provided by the pressure sensor and/or the flow sensor by means of a memory associated with the control unit and arranged in or at the control unit.

In interaction with the memory, the control unit is preferably also configured to store the measured values detected and provided by the gas sensor system. In addition, the control unit is configured to coordinate the pumping device by means of a sequence of steps in order to test the operational capability of the gas guide element and to determine an indicator of the operational capability of the gas guide element.

The control unit may be configured according to the present invention in the testing device with the pumping device for testing the operational capability of a gas guide element of a gas-measuring system as an independent unit as well as an element of the pumping device, of the test gas source or of the gas sensor system.

The control unit may further be configured as a distributed control, configured, for example, as a combination of different computers ($\mu$P, $\mu$C) in the gas-measuring system, distributed, for example, among the pumping device, the test gas source, an independent calculation and control unit, as well as part of the gas sensor system.

The operational capability of the gas guide element is tested by means of the control unit, which controls or regulates the pumping device and actuators, preferably a pump, such as pump drives, diaphragm pumps, piezo pumps, reciprocating pumps, compressor pumps and switching elements, preferably valves, solenoid valves, electromagnetic valves, 2/2-way valves, 2/3-way valves, which are arranged in or at the pumping device or are associated with the pumping device and are suitable for delivering gas, in terms of the functions of the pumping device, namely, delivery pressure, flow rates with direction and quantities and duration of delivery, including suitable sensor systems (pressure, flow, temperature, humidity), which are arranged at the pumping device or are associated with the pumping device.

The system variable, which represents differences in the density and/or in the dynamic viscosity, is used by the control unit in a testing procedure for testing the operational capability of the gas guide element.

A configuration of the control of the pump may be embodied, for example, by the pump being regulated to a constant speed of rotation. Due to the density and/or viscosity differences of the test gas against the ambient air, there will be changes over time in the measured values of the pressure sensor and/or changes in the measured values of the flow sensor during the testing in such a case as changes of the system variable, which represents differences in the density and/or in the dynamic viscosity of the test gas. There also are changes in such a case in the actuating signal of the pump or in the electric current consumption or electric power consumption as changes of the system variable.

In the course of the testing procedure for testing the operational capability of the gas guide element, the control unit carries out a sequence of steps, in the course of which a quantity of test gas is delivered by means of the pumping device from or out of the pumping device to the remotely located measuring location and is subsequently delivered again from the remotely located measuring location back into or to the pumping device.

The control unit carries out for this the following sequence of steps, which represents a general procedure, in order to carry out the testing of the operational capability of the pumping device with inclusion of the system variable.

In a first step, the control unit brings the pumping device into a first operating state for a first, predefined time period. A quantity of test gas is delivered in the first operating state from the test gas source to a remotely located measuring location by means of the gas guide element.

The duration of the first predefined time period is configured by the control unit on the basis of technical properties of the gas guide element and on the basis of technical properties of the pumping device such that the gas guide element is filled with the test gas over a length from the remotely located measuring location to the pumping device. The gas guide element is thus filled completely with the test gas with a total gas volume of the gas guide element over a length from the remotely located measuring location to the pumping device. The technical properties of the pumping device comprise essentially the characteristics of the actuators (pumps) and switching elements (valves) arranged in the pumping device, such as flow rate and pressurized dispensing ranges, which the pumping device provides for delivering the quantity (delivery rate) of test gas from the test gas source by means of the gas guide element to the remotely located measuring location in the first operating state. Furthermore, the technical properties of the pumping device also comprise the type of arrangement of the test gas source at the pumping device, i.e., dimensions, such as length and flow cross section of a partial section of the gas guide element arranged and intended therefor.

In addition, the technical properties of the pumping device also comprise the manner of control, i.e., of the control or regulation of the pump in the pumping device, as if, for example, the speed of rotation of the pump were adjusted in the pumping device according to a delivery pressure predefined or detected with the pressure sensor and/or according to a predefined flow rate or a flow rate detected with the flow sensor.

The technical properties of the gas guide element comprise here dimensions, such as an overall length from the pumping device and/or the gas sensor system to the remotely located measuring location, a line diameter belonging to the overall length of the gas guide element, so that a total gas volume present in the gas guide element can be determined from this by the control unit. However, the technical properties of the gas guide element may also comprise the technical properties of individual parts of the gas guide element, i.e., flow cross sections and lengths of different line sections of the gas guide element, in case of a multipart gas guide element. In addition, information on the material, wall thickness, geometric shape (round, elliptical, square), as well as information on a difference in level between the remotely located measuring location and the pumping device or the gas sensor system may also be included in the technical properties of the gas guide element. Knowing the technical properties of the individual parts of the gas guide element, the control unit is able to also determine the total gas volume of the multipart gas guide element. The predefined time period so that a quantity of test gas is delivered from the test gas source to the gas guide element in the direction toward the remotely located measuring location may advantageously be based on the at least one or more of the technical properties as comprising at least flow rate of the pump, line length and flow cross section/line diameter.

The first predefined time period is selected by the control unit such that the quantity of test gas delivered by the pumping device into the gas guide element toward the remotely located measuring location at the flow rate arising from the technical properties of the pumping device fills the entire gas volume of the gas guide element during the first predefined time period. If, for example, the gas guide element has a gas volume of 5 L over the length of the gas guide element between the pumping device and the remotely located measuring location, the gas guide element is completely filled with the test gas between the pumping device and the remotely located measuring location at a set delivery rate of 0.5 L per minute, which is provided by the pumping device, after a duration of 10 minutes, the gas volume in a partial gas guide element, which connects the test gas source with the pumping device, being ignored in this simplified view.

The pumping device is put by the control unit into a second operating state for a second predefined time period. A quantity of gas is delivered in the second operating state from the remotely located measuring location to the pressure sensor and/or to the flow sensor in the gas-measuring system by means of the gas guide element.

The duration of the second predefined time period is selected by the control unit on the basis of the first predefined time period and on the basis of technical properties of the gas guide element and/or on the basis of technical properties of the pumping device. The technical properties of the pumping device comprise characteristics of the actuators (pumps) and switching elements (valves) arranged in the pumping device, such as flow rate and pressurized dispensing ranges, which the pumping device provides for delivering the quantity of gas (delivery rate) from the remotely located measuring side of the gas guide element in the second operating state. In addition, the technical properties of the pumping device also comprise the type of arrangement of the gas sensor system at the pumping device, i.e., dimensions, such as length and flow cross section of a section of the gas guide element, which is arranged and intended for this. In one constellation, in which the technical properties of the pumping device are nearly identical for the delivery rate from the remotely located measuring location to the pumping device and for the direction of delivery from the test gas source to the remotely located measuring location because, for example, the same pump is used with switchover of the direction of delivery by means of a device comprising two 3/2-way valves coupled by the control unit in the control, the second predefined time period nearly corresponds to the first predefined time period if switchover times of the valves and the duration needed for the delivery of gas by the pumping device to the gas sensor system is ignored. If, for example, the gas guide element has a gas volume of 5 L over the length of the gas guide element between the remotely located measuring location and the pumping device, the gas guide element is completely filled with gas between the remotely located measuring location and the pumping device in case of a delivery rate of 0.25 L per minute, which is set and provided by the pumping device, after a duration of 20 minutes. In order for the gas being delivered from the remotely located measuring location to be able to reach the gas sensor system, the delivery of the gas must be continued for an additional time period, which is, however, comparatively short compared to the second predefined time period, and the gas volume in a gas guide element, which connects the gas sensor system to the pumping device, must additionally also be taken into account during this additional time period. The duration of the second predefined time period thus also comprises the duration that is necessary for the delivery of the gas volume in the gas guide element, which connects the gas sensor system to the pumping device, from the pumping device to the gas sensor system at a set delivery rate. If the gas volume in the gas guide element, which connects the gas sensor system with the pumping device, has a volume of, for example, 0.05 L, an additional time period of 1/5 minute, i.e., 12 sec, is also to be taken additionally into account in the second predefined time period at a set delivery rate of 0.25 L per minute, which is provided by the pumping device.

The control unit receives a plurality of measured values, which are provided by the pressure sensor and/or the flow sensor, during the second predefined time period, and it uses these measured values to monitor the function of the pump or to control the pump by means of control or regulation.

In the second step, at the beginning of the second predefined time period, the control unit stores in the memory a first value of the system variable, which value represents a current density and/or dynamic viscosity of the gas or gas mixture (test gas) present in the gas guide element, as a first comparison data value.

In the second step at the end of the second predefined time period, the control unit determines another value of the system variable, which represents a then current density and/or dynamic viscosity in the gas guide element, and stores this value as a second comparison data value in the memory.

In a third step, the control unit performs a comparison between the first comparison data value and the second comparison data value and determines an indicator of the operational capability of the gas guide element on the basis of the comparison between the first comparison data value and the second comparison data value and of a predefined comparison criterion. Based on this comparison, the control unit can determine whether the quantity of test gas delivered in the first operating state to the remotely located measuring location has been delivered in the second operating state as a quantity of gas from the remotely located measuring location to the gas sensor system. If the first comparison data value and the second comparison data value show hardly any deviations from one another, the result of the comparison is that the quantity of test gas delivered to the remotely located measuring location is identical in volume to the quantity of gas that was delivered from the remotely located measuring location to the gas sensor system.

In such a case, it is obtained as the basis for the indicator of the operational capability of the gas guide element that the gas guide element is classified by the control unit as being capable of operating, i.e., there also are no significant leaks or leakages over the entire length of the gas guide element from the remotely located measuring location to the pressure sensor and hence at the gas sensor system in case the pressure sensor or the flow sensor are arranged close to the gas sensor system in space.

If the second comparison data value is different from the first comparison data value if the predefined comparison criterion is used, the situation arises that the gas guide element is not capable of functioning, i.e., leaks are present.

The predefined comparison criterion may now be configured such that the indicator of the operational capability of the gas guide element is put into the "capable of operating" state if the result of the comparison between the first comparison data value and the second comparison data value shows that the difference between the first comparison data value and the second comparison data value is less than a predefined difference, for example, <5%.

Depending on the configuration of the gas guide element and the complexity of the arrangement of the gas guide elements and connection elements and depending on the density and the viscosity of the test gas used—see Table 1 and Table 2—a range of 1% to 10% may be practicable as a predefined comparison criterion for the testing of the operational capability of the gas guide element.

If, for example, xenon with a density of $?=5.89$ kg/m$^3$ at an ambient temperature of 0° C. and at an ambient pressure of 1,013 hPa is used as the test gas, the difference in density between ambient air (oxygen ~21%, nitrogen ~78%, water vapor, carbon dioxide, noble gases) with a density of $\rho=1.29$ kg/m$^3$ at an ambient temperature of 0° C. and an ambient pressure of 1,013 hPa and the test gas is approx. 70%. A predefined comparison criterion in the range of 1% to 10% relative to the system size, which represents differences in the density and/or in the dynamic viscosity of the test gas, is readily applicable, because even a constellation of a gas mixture of about 10% xenon in ambient air can thus still be determined sufficiently well as a difference by the control unit.

This first example, related to the density, can also be applied to a difference in the density between ambient air and helium, as it is shown in Table 1. The difference in density equals about 90% between helium with $\rho=0.18$ kg/m$^3$ and ambient air, so that even a predefined comparison criterion in the range markedly above 8% can now be used, relative to the system size, which represents differences in the density and/or in the dynamic viscosity of the test gas, for helium concentrations of less than 25% in the test gas.

The examples related to the density can also be applied to the differences in the viscosity (see Table 2) concerning the effect on the measured value of the pressure and the selection of the predefined comparison criterion. If, for example, neon is used as the test gas, a viscosity difference of 82% is obtained against ambient air, so that a predefined comparison criterion in a range of 1% to 10% relative to the system size, which represents differences in the density and/or in the dynamic viscosity of the test gas, can be considered to be meaningful here as well.

If, for example, xenon is again used as the test gas, a viscosity difference of about 29% is obtained (see Table 2).

If xenon is used as the test gas, the special advantage arises that the properties in terms of the density and the viscosity of xenon make it possible to carry out the testing of the operational capability of the gas guide element nearly independently from the configuration of the above-described variants of the pump control in the pumping device.

The control unit determines, in a fourth step, an output signal, which indicates the indicator of the operational capability of the gas guide element, on the basis of the indicator of the operational capability of the gas guide element, and provides this output signal.

In a preferred embodiment, measured values provided by the sensor, which indicates the state of flow in the gas guide element or an operating state of the pumping device, are used according to the first configuration of the system size by the control unit in the testing procedure for testing the operational capability of the gas guide element.

In an especially preferred configuration of the first embodiment of the system size, measured values of the pressure sensor are used by the control unit in the testing procedure for testing the operational capability of the gas guide element.

In an alternative preferred configuration of the first embodiment of the system size, measured values of the flow sensor are used by the control unit in the testing procedure for testing the operational capability of the gas guide element.

According to the especially preferred configuration of the first embodiment of the system size, the control unit carries out for this the following sequence of steps with inclusion and assessment of the measured values provided by the pressure sensor:

In a first step, the control unit puts the pumping device into a first operating state for a first predefined time period. A quantity of test gas is delivered in the first operating state from the test gas source to a remotely located measuring location by means of the gas guide element. The duration of the first predefined time period is configured by the control unit on the basis of technical properties of the gas guide element and on the basis of technical properties of the pumping device in a manner already described before in different individual aspects in the description of the general procedure with inclusion of the system size for testing the operational capability of the pumping device. The technical properties of the pumping device, which were taken into account, comprise here the aspects that were already described before in the description of the principal procedure with inclusion of the system size for testing the functional capability of the pumping device.

The pumping device is put by the control unit into a second operating state for a second predefined time period in a second step. A quantity of gas is delivered in the second operating state from the remotely located measuring location to the pressure sensor and to the gas-measuring system by means of the gas guide element.

The duration of the predefined time period is configured by the control unit on the basis of the first predefined time period and on the basis of technical properties of the gas guide element in a manner as already described before in different individual aspects in the description of the general procedure with inclusion of the system size for testing the operational capability of the pumping device. The technical properties of the pumping device, which are taken into account, comprise here the aspects that were already described before in the description of general procedure with inclusion of the system size for testing the operational capability of the pumping device.

During the second predefined time period, the control unit receives a plurality of measured values provided by the pressure sensor. The control unit stores a then current measured value of the provided measured values as a first comparison data value in the memory in the second step at the beginning of the second predefined time period. The control unit stores in the memory another, then current measured value of the provided measured values as a second comparison data value.

In a third step, the control unit performs a comparison between the first comparison data value and the second comparison data value and determines an indicator of the operational capability of the gas guide element on the basis of the comparison between the first comparison data value and the second comparison data value and of a predefined comparison criterion. Based on this comparison, the control unit determines, as was described before in the description of the general procedure with inclusion of the system size for testing the operational capability of the pumping device, an indicator of the operational capability of the gas guide element. The predefined comparison criterion may have a configuration comparable to what was described above in the description of the general procedure with inclusion of the system size for testing the operational capability of the pumping device.

In a fourth step, the control unit determines, on the basis of the indicator of the operational capability of the gas guide element, an output signal, which indicates the indicator of the operational capability of the gas guide element and provides this output signal.

According to the alternative configuration of the first embodiment of the system size, the control unit performs for following sequence of steps with inclusion and assessment of the measured values provided by the flow sensor:

The control unit puts the pumping device into a first operating state for a first predefined time period a first step. A quantity of test gas is delivered in the first operating state from the test gas source toward a remotely located measuring location by means of the gas guide element. The duration of the first predefined time period is configured by the control unit on the basis of technical properties of the gas guide element and on the basis of technical properties of the pumping device in a manner as was already described above in different individual aspects in the description of the general procedure with inclusion of the system size for testing the operational capability of the pumping device. The technical properties of the pumping device, which are taken into account, comprise here the aspects that were already described above in the description of general procedure with inclusion of the system size for testing the operational capability of the pumping device.

In a second step, the pumping device is put by the device into a second operating state for a second predefined time period. A quantity of gas is delivered in the second operating state from the remotely located measuring location to the flow sensor and to the gas-measuring system by means of the gas guide element.

The duration of the second predefined time period is configured by the control unit on the basis of the first predefined time period and on the basis of technical properties of the gas guide element and/or on the basis of technical properties of the pumping device in a manner as was already described above in different individual aspects in the description of the general procedure with inclusion of the system size for testing the operational capability of the pumping device. The technical properties of the pumping device, which are taken into account, comprise here the aspects that were already described before in the description of the general procedure with inclusion of the system size for testing the operational capability of the pumping device.

During the second predefined time period, the control unit receives a plurality of measured values provided by the flow sensor. The control unit stores a then current measured value of the provided measured values as a first comparison data value in the memory in the second step at the beginning of the second predefined time period. The control unit stores another, then current measured value of the provided measured values as a second comparison data value in the memory in the second step at the end of the second predefined time period.

In a third step, the control unit performs a comparison between the first comparison data value and the second comparison data value and determines an indicator of the operational capability of the gas guide element on the basis of the comparison between the first comparison data value and the second comparison data value. Based on this comparison, the control unit determines, as was mentioned before in the description of the general procedure with inclusion of the system size for testing the operational capability of the pumping device, an indicator of the operational capability of the gas guide element. The predefined comparison criterion may now be comparable to what was described before in the description of the general procedure with inclusion of the system size for testing the operational capability of the pumping device.

In a fourth step, the control unit determines an output signal, which indicates the indicator of the operational capability of the gas guide element on the basis of the indicator of the operational capability of the gas guide element and provides this output signal.

According to the further configuration of the system size, parameters, which indicate operating states of the pump, are used in the testing procedure for testing the operational capability of the gas guide element in a preferred embodiment of the control unit. The operating states of the pump are obtained indirectly with the control of the pump from changes in the dynamic viscosity and/or the density of the test gas, which directly affect changes in the measured values of the pressure.

Since such changes in the measured values of the pressure have an effect in a regulation of the pump with the regulation target of a constant delivery pressure then lead to changes of at least one parameter indicating the operating state of the pump, this parameter can be assessed by the control unit as an indication for a change in the dynamic viscosity and/or the density of the test gas. The parameter due to changes in the dynamic viscosity and/or the density of the test gas are measurable as short-term deviations of the measured values of the pressure from a set point of the delivery pressure for only a duration that is necessary in the control circuit for the adjustment until the set point of the delivery pressure is reached. This duration depends on the control system, which includes, for example, the length and the volume of the gas guide element, as well as on the type of the controller in terms of type (P, I, D, PD, PI, PID, as well as two-point controllers, three-point controllers, three-point step controllers) and the configuration thereof ($T_t$, $T_e$, $T_b$, $T_i$, $T_d$ and hysteresis, switching difference). A plurality of parameters, which indicate operating states of the pump and go indirectly back to changes in the dynamic viscosity and/or the density of the test gas, are available to the control unit. The parameters available to the control unit are operating parameters of the pump, for example, electrical actuating signals, such as electrical pump output, electric power consumption, and PWM actuating signal. Further parameters are speed of rotation, flow rate or pressure. The speed of rotation may be provided for the control unit, for example, by means of an internal sensor system of the pump, configured, for example, as a Hall sensor. The flow rate may be configured as a delivery rate, in addition to the delivery pressure, by means of a flow sensor, configured, for example, as a pressure difference sensor with a diaphragm or by means of a laminar flow element (LFE) or as a flow sensor (hot-wire or hot-film anemometer, thermoelectric MEMS sensor) operating according to the measuring principle of heat transport, as well as an ultrasonic flow sensor or impeller flow sensor (rotameter, impeller). Depending on the configuration of the control with controlling or regulating the pump and on the additional sensor system used, at least one parameter is obtained in the interaction between pump output, power consumption, PWM actuating signal, speed of rotation, flow rate and pressure, which parameter represents as an operating state differences in the density and/or in the dynamic viscosity of the test gas.

The control unit performs for this the following sequence of steps with inclusion and assessment of at least one of the parameters, which indicate operating states of the pump:

In a first step, the control unit puts the pumping device into a first operating state for a first predefined time period. A quantity of test gas is delivered in the first operating state from the test gas source to a remotely located measuring location by means of the gas guide element. The duration of the first predefined time period is configured by the control unit on the basis of technical properties of the gas guide element and on the basis of technical properties of the pumping device in such a manner as was already described before in the description of the general procedure with inclusion of the system size for testing the operational capability of the pumping device. The technical properties of the pumping device, which are taken into account, comprise here the aspects that were already described before in the description of the general procedure with inclusion of the system size for testing the operational capability of the pumping device.

In a second step, the pumping device is put by the control unit into a second operating state for a second predefined time period. A quantity of gas is delivered in the second operating state by means of the gas guide element from the remotely located measuring location to the sensor, which indicates the state of flow in the gas guide element or an operating state of the pumping device, and to the gas-measuring system. The duration of the second predefined time period is configured by the control unit on the basis of the first predefined time period and on the basis of technical properties of the gas guide element and/or on the basis of technical properties of the pumping device in a manner as was already described before in different individuals aspects in the description of the general procedure with inclusion of the system size for testing the operational capability of the pumping device. The technical properties of the pumping device, which are taken into account, comprise here the aspects that were already described before in the description of the general procedure with inclusion of the system size for testing the operational capability of the pumping device. The control unit stores a value of at least one, then current parameter as a first comparison data value in the memory in the second step at the beginning of the second predefined time period. The control unit stores in the memory another value of at least one, then current parameter as a second comparison data value in the second step at the end of the second predefined time period. The parameters available to the control unit are operating parameters of the pump, for example, electrical actuating signals, such as the electrical output of the pump, electric power consumption, PWM actuating signals. Additional parameters are the speed of rotation, flow rate or pressure. Depending on the configuration of the control with controlling or regulating the pump, at least one parameter is obtained as a system variable, which represents differences in the density and/or in the dynamic viscosity of the test gas, in the interaction between the pump output, power consumption, PWM actuating signal, speed of rotation, flow rate and pressure.

In a third step, the control unit performs a comparison between the first comparison data value and the second comparison data value and determines an indicator of the operational capability of the gas guide element on the basis of the comparison between the first comparison data value and the second comparison data value and of a predefined comparison criterion. Based on this comparison, the control unit determines, as was already described before in the description of the general procedure with inclusion of the system size for testing the operational capability of the pumping device, an indicator of the operational capability of the gas guide element. The predefined comparison criterion may now have a configuration similar to that already described before in the description of the general procedure with inclusion of the system size for testing the operational capability of the pumping device.

In a fourth step, the control unit determines an output signal, which indicates the indicator of the operational capability of the gas guide element, on the basis of the indicator of the operational capability of the gas guide element, and provides this output signal.

In a preferred embodiment, a scavenging gas source is arranged at the pumping device. The scavenging gas source is arranged at the pumping device and the gas guide element, the gas sensor system and the pumping device are connected fluidically to one another such that a quantity of scavenging gas can be fed to the gas sensor as a quantity of gas from the scavenging gas source.

In the first operating state, before the control unit sets the pumping device in the first step into the first operating state, in which the quantity of test gas is delivered from the test gas source to the remotely located measuring location by means of the gas guide element, for the first predefined time period, the pumping device is set by the control unit into an expanded operating state for the first predefined time period. A quantity of scavenging gas is delivered in the expanded operating state from the scavenging gas source to the remotely located measuring location by means of the gas guide element, so that the gas guide element is completely filled with the scavenging gas over the length from the remotely located measuring location to the pumping device.

The expanded operating state corresponds here, in the configuration of the predefined time period as well, to the first operating state of the testing device according to the present invention for testing the operational capability of a gas guide element of a gas-measuring system. The first predefined time period may also be called a scavenging time period in this expanded operating state. This scavenging time period is selected by the control unit such that the quantity of scavenging gas delivered fills the entire gas volume of the gas guide element with the set flow rate or delivery rate during the scavenging time period.

In a preferred embodiment of the testing device, the test gas source and/or the scavenging gas source are configured as a configuration of a container in combination with an array of valves, switching devices or piezo dispensing elements. The valves, switching devices or piezo dispensing elements can be activated by the control unit by means of control signals such that the test gas and/or the scavenging gas is provided for, sent or fed to the pumping device.

In a preferred embodiment of the pumping device, the pumping device is equipped with a bidirectional pump. The direction of delivery of this bidirectionally delivering pump can be reversed by the control unit by means of a control signal such that either a quantity of measured gas is delivered from the remotely located measuring location to the pumping device and to the gas sensor, or a quantity of test gas is delivered from the test gas source to the remotely located measuring location. The direction of delivery is preferably reversed here, for example, directly by means of a switchover of the direction of rotation of the pump motor by the control unit. Such a direct reversal of the direction of delivery by means of the pump has the advantage that only a single pump is necessary without the need for additional arrays of valves in the testing device for testing the operational capability of the gas guide element.

In another preferred embodiment of the testing device, the pumping device is provided with a pump, whose direction of delivery can be set indirectly by means of an array of two so-called 3/2-way valves by the control unit by means of control signal. Respective states of flow of the two 3/2-way valves can be set by the control unit by means of the control signals such that either a quantity of gas is delivered from the remotely located measuring location to the pumping device and to the gas sensor, or a quantity of gas is delivered from the test gas source to the remotely located measuring location.

Such a reversal of the direction of delivery by means of the valve array has the advantage that only one, comparatively simple pump with a permanently preset possible direction of delivery is necessary. In addition, the array of valves ensures that the flow directions within the pumping device, as well as in the gas guide element to the gas sensor and from and to the remotely located measuring location are also defined without an actuation by the control unit by the resting position of the valves. This makes possible a reliable operation of the pumping device in a simple manner without complicated monitoring of the pump and the operation thereof, such as, for example, the direction of delivery of the pump.

In a preferred embodiment of the testing device, the testing device is equipped with an array of two pumps in an antiparallel arrangement. The control unit can bring about mutual activation of one or the other of the pumps by means of a control signal and thus reverse the direction of delivery in the pumping device such that either a quantity of measured gas is delivered from the remotely located measuring location to the pumping device or to the gas sensor, or a quantity of test gas is delivered from the test gas source to the remotely located measuring location. Such a reversal of the direction of delivery by means of two pumps has the advantage that only one pump must be activated by the control unit, so that the directions of delivery can be changed over by the control unit smoothly, without switchover times of valves having to be taken into account as well.

In a preferred embodiment of the testing device, a gas outlet is arranged in the testing device and a 3/2-way valve, whose state of flow can be set by the control unit by means of a control signal such that delivery of a quantity of gas from the remotely located measuring location to the gas sensor or delivery of the quantity of gas from the remotely located measuring location into the gas outlet is ensured. The arrangement of the gas outlet with the associated 3/2-way valve offers, for example, the advantage that scavenging of the pumping device as well as of the gas guide element with the scavenging gas can be carried out without the scavenging gas having to be fed to the gas sensor. This offers the advantage that there are no waiting times or recovery times of the gas sensor system for the detection of the measured gas during the further measuring operation by the gas sensor following the scavenging of the gas guide element. Another advantage offered by the 3/2-way valve and the gas outlet arises from the fact that the gas sensor can be uncoupled from scavenging gas, measured gas or test gas at any time during the testing of the operational capability of the gas guide element by the control unit by means of a control signal, so that, for example, a testing, resetting, adjustment (offset, characteristic) or calibration of the gas sensor system can also be carried out or prompted by the control unit during the ongoing testing of the operational capability of the gas guide element.

In a preferred embodiment, a 2/2-way valve, whose state is controlled by means of a control signal of the control unit such that test gas or scavenging gas is delivered as a quantity of gas to the remotely located measuring location and no test gas and no scavenging gas is delivered to or can reach the gas sensor directly from the test gas source or from the pumping device, is arranged in or at the pumping device, the test gas source or the scavenging gas source. The control unit is thus enabled to ensure in all cases when and for what duration the test gas or the scavenging gas can reach the remotely located measuring location from the test gas source or the pumping device. This ensures that no undefined gas mixtures are present in the gas guide element even if pumps that are not activated are not closed completely against the direction of delivery.

In a preferred embodiment of the testing device, a gas generator is arranged as a test gas source at the pumping device. The gas generator is activated by means of a control signal by the control unit and generates test gas electrolytically, chemically or electrochemically. For example, hydrocarbons, e.g., ethane, can be produced with gas generators.

In a preferred embodiment, the test gas source is configured as a pressure tank, in which the test gas is stored under an admission pressure in the liquid form and is provided for delivery to the remotely located measuring location. A shut-off valve, usually configured as a 2/2-way valve, which is activated by the control unit to allow the test gas being stored in liquid form under admission pressure into the gas guide element, is arranged in the pumping device. A pressure release occurs during the inflow, so that the test gas flows into the gas guide element in the gaseous form. Suitable test gases for storage under pressure are, for example, propane, butane, and propane/butane mixtures. In an embodiment with a test gas that is under admission pressure, a pump is not necessary in all applications for the delivery of the test gas to the remotely located measuring location in the testing device for testing the operational capability of the gas guide element. A pump is necessary only when a greater distance must be covered from the pumping device to the remotely located measuring location for delivering the test gas to the remotely located measuring location or when a greater level difference must be overcome from the pumping device to the remotely located measuring location, whether the remotely located measuring location is located at a markedly higher elevation than the pumping device or the test gas source or the remotely located measuring location is located at a markedly lower elevation than the pumping device or the test gas source. This happens, for example, in applications in which the distance—and hence the length of the gas guide element—is greater than 15 m or a difference greater than 10 m in elevation must be overcome. The delivery of the test gas to the remotely located measuring location is otherwise brought about and made possible by the admission pressure of the test gas as an inflow on the basis of the pressure difference between the pressure tank and the measuring location. The control unit can thus bring about the flow to the remotely located measuring location by means of a control signal for activation of the shut-off valve (2/2-way valve) by the control signal.

The pump or pumps described in the embodiments of the pumping device is/are preferably controlled, for example, in terms of the delivery rate and/or the flow rate and/or the delivery pressure of the pump, via the speed of rotation n of a pump motor provided in or at the pump for driving the pump. The control of the delivery rate, flow rate or delivery pressure is defined in the sense of the present invention as any kind of external influence by means of setting, adjusting, controlling or regulating the pump in terms of its speed of rotation n, the delivery pressure, the flow rate or the delivery rate. An electrically operated pump motor may be controlled by the control unit, for example, according to a speed of rotation characteristic or speed of rotation-flow characteristic by means of control signal configured as a d.c. signal or as a pulse-width modulated signal (PWM).

In a preferred embodiment of the testing device, the sensor, which indicates the state of flow in the gas guide element or an operating state of the pumping device, are used by the control unit to control the delivery rate and/or the flow rate of the pump or pumps in the pumping device by means of a control signal on the basis of the measured values of the sensor, which indicates the state of flow in the gas guide element or an operating state of the pumping device.

In a preferred embodiment of the testing device, the pressure sensor and/or the flow sensor and/or the speed of rotation sensor are used by the control unit to control the delivery rate and/or the flow rate of the pump or pumps in the pumping device by means of a control signal on the basis of the measured values of the pressure sensor and/or of the measured values of the flow sensor and/or of the measured values of the speed of rotation sensor.

The embodiments described represent both in themselves and in combination or combinations with one another special embodiments of the testing device for testing a gas guide element. All and possible additional embodiments and their advantages arising from a combination or combinations of a plurality of embodiments are likewise also covered by the inventive idea, even if not all the combination possibilities of embodiments are specifically described for this in detail.

The present invention will now be described in more detail by means of the following figures and the corresponding description of the figures without limitation of the general inventive features. The present invention will be described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1b is a schematic view of a second variant of the pumping device according to FIG. 1a;

DESCRIPTION OF THE PREFERRED EMBODIMENTS

Figure 1A:
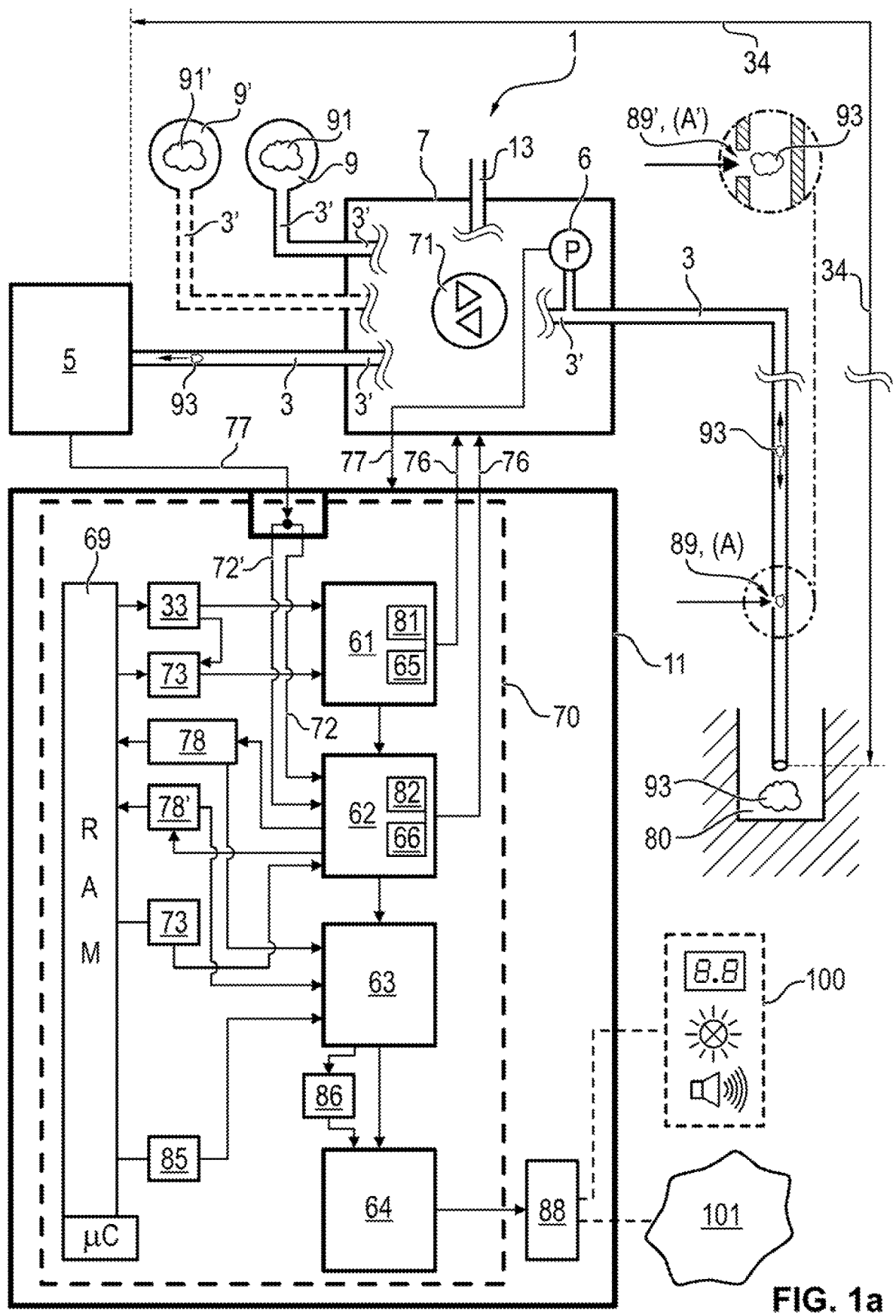
FIG. 1a is a schematic view of a testing device with a first variant of a pumping device for testing the operational capability of a gas guide element.

Referring to the drawings, FIG. 1a shows a schematic view of a testing device 1 with a first variant of a pumping device 7 for testing the operational capability of a gas guide element 3 in a gas-measuring system 11.

The testing device 1 tests the operational capability of the gas guide element 3 in the gas-measuring system 11. The gas-measuring system 11 has a gas sensor 5, a pressure sensor 6, a pumping device 7, and the gas guide element 3. The testing device 1 comprises a test gas source 9, and a control unit 70 with an associated memory 69. The control unit 70 has connections (signal line connections) to the pumping device 7 and the gas sensor 5 and the pressure sensor 6. The control unit 70 may be a part of the system 11 and may be configured as described below to provide the control features of the test device 1. The gas sensor system 5, the pumping device 7, and the gas guide element 3 also provide features of the testing device 1.

The testing device 1 for determining the operational capability of the gas guide element 3 is shown in this FIG. 1a in a global context of an application in the gas-measuring system 11. The gas-measuring system 11 has a remotely located measuring location 80, from which gas is delivered via the gas guide element 3 by means of the pumping device 7 to the gas sensor 5 and thus also to the pressure sensor 6. The remotely located measuring location 80 may be, for example, a tank, a silo, a shaft, a tunnel, as well as a tank on a motor vehicle, a tank on a ship or a storage room on a ship. The situation that maintenance personnel must be able to assess the situation concerning a gas concentration that is hazardous to health in such a tank, silo or storage location by means of a prior measurement is characteristic of the remotely located measuring location 80. A quantity of gas 93 is delivered for this by means of the gas guide element 3 from this tank or silo to the gas sensor 5. It is important for the gas guide element to be able to function, i.e., intact and free from leaks over an entire length 34 from the remotely located measuring location 80 to the gas sensor 5 for this delivery of the quantity of gas 93. The pumping device 7 is therefore configured in this FIG. 1a to deliver not only quantities of gas 93 from the remotely located measuring location 80 to the gas sensor 5, but also quantities of gas 93 as test gas 91 from the test gas source 9 to the remotely located measuring location 80. The gas guide element 3 is flooded or filled with the test gas during this delivery over the length 34 from the remotely located measuring location 80 into the pumping device 7. The volume of test gas 91, which was just delivered into the gas guide element 3, is delivered back again into the pumping device 7 during the subsequent delivery from the remotely located measuring location 80 and is fed by the pumping device 7 to the pressure sensor 6 for an analysis of changes in the density and/or the dynamic viscosity over time of the return delivery of the test gas 9. When measured values 77 of the pressure sensor 6 are then analyzed with the pressure sensor 6 at the beginning of the return delivery as well as at the end of the return delivery, operational capability of the gas guide element 3 can be inferred.

If no change occurs in the measured values between the measured values measured at the beginning of the return delivery and the measured values measured at the end of the return delivery, it can be inferred that no leakage or leak 89, from which a quantity of gas 93 could escape from the gas guide element 3, for example, into the ambient air, is present in the gas guide element 3.

The gas guide element 3 is arranged between the pumping device 7, the pressure sensor 6 and the gas sensor 5. The gas guide element 3, the pressure sensor 6, the gas sensor 5, and the pumping device 7 are connected to one another fluidically and configured for an interaction such that a quantity of gas 93 can be fed to the pressure sensor 6 and to the gas sensor 5 from a remotely located measuring location 80 and the quantity of gas 93 can be fed from the pumping device 7 to the remotely located measuring location 80.

A location A 89 of a possible leak is shown on the gas guide element 3 in this FIG. 1a. In addition, the leak A 89 is shown as an enlarged detail A' 89' with the quantity of gas 93 as a leakage (leak) in the wall of the gas guide element 3.

The test gas source 9 is arranged in or at the pumping device 7 and the gas guide element 3, the gas sensor 5 and the pumping device 7 are connected to one another fluidically such that a quantity of test gas 91 can be fed as a quantity of gas 93 to the remotely located measuring location 80 from the test gas source 9.

This FIG. 1a schematically shows in the pumping device 7 a bidirectionally delivering pump 71, which can be activated by means of the control unit 70 for delivering quantities of gas 93 from the pumping device 7 to the remotely located measuring location and from the remotely located measuring location 80 by means of a control signal 76.

Figure 2A:
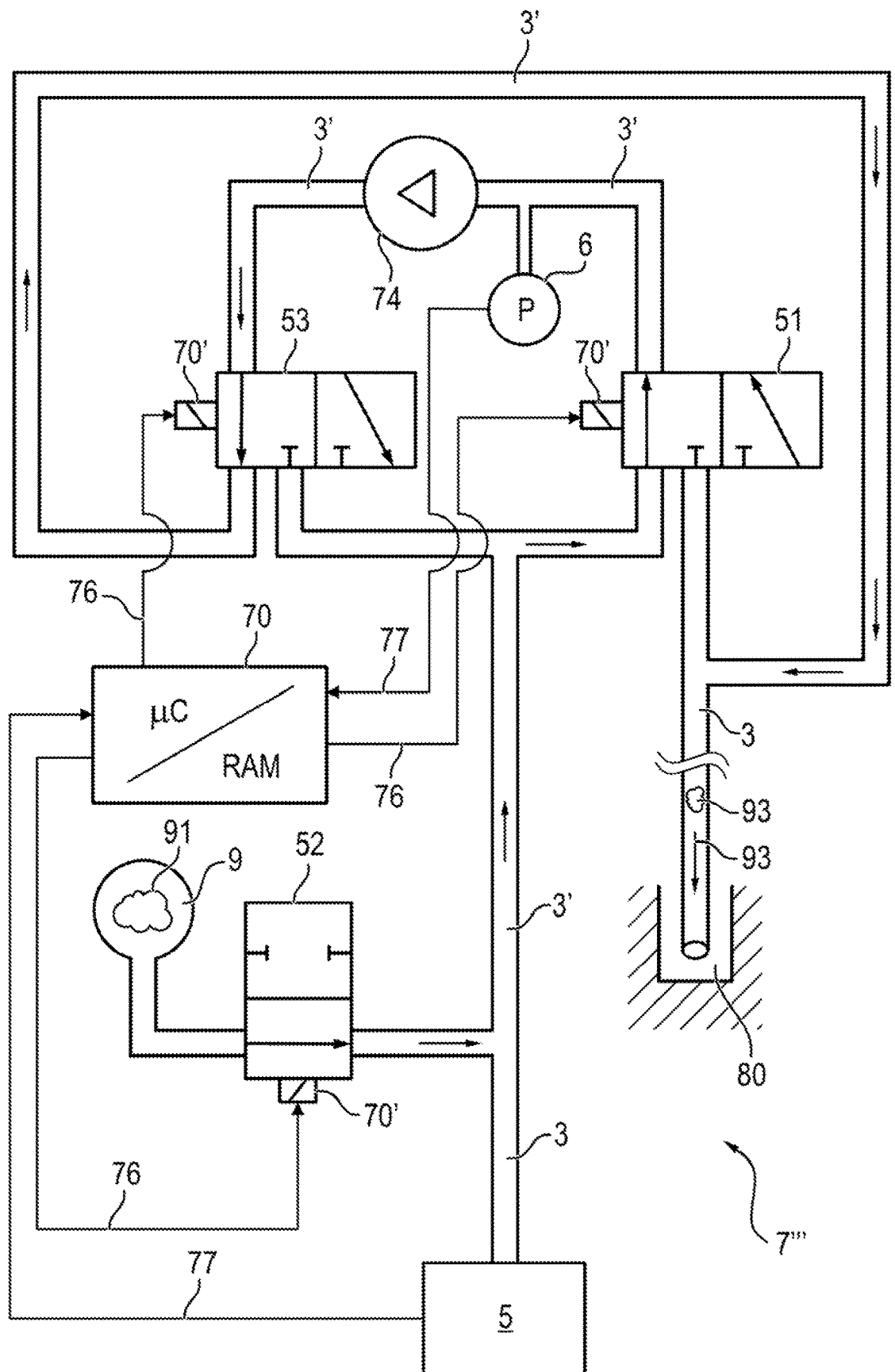
FIG. 2a is a schematic view of a third variant of the pumping device according to FIG. 1a in a first operating state.
Figure 2B:
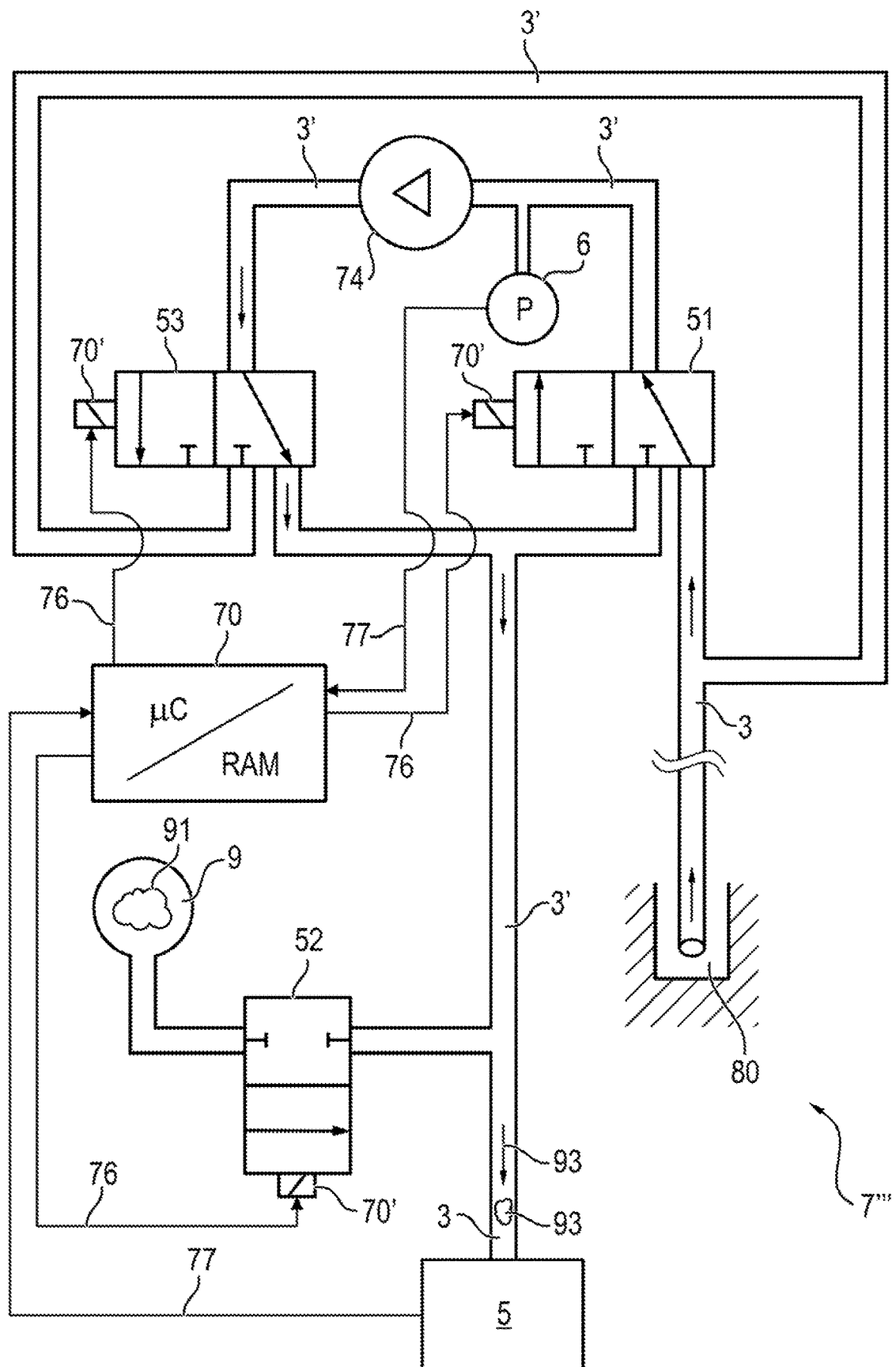
FIG. 2b is a schematic view of the third variant of the pumping device according to FIG. 1a in a second operating state.
Figure 3A:
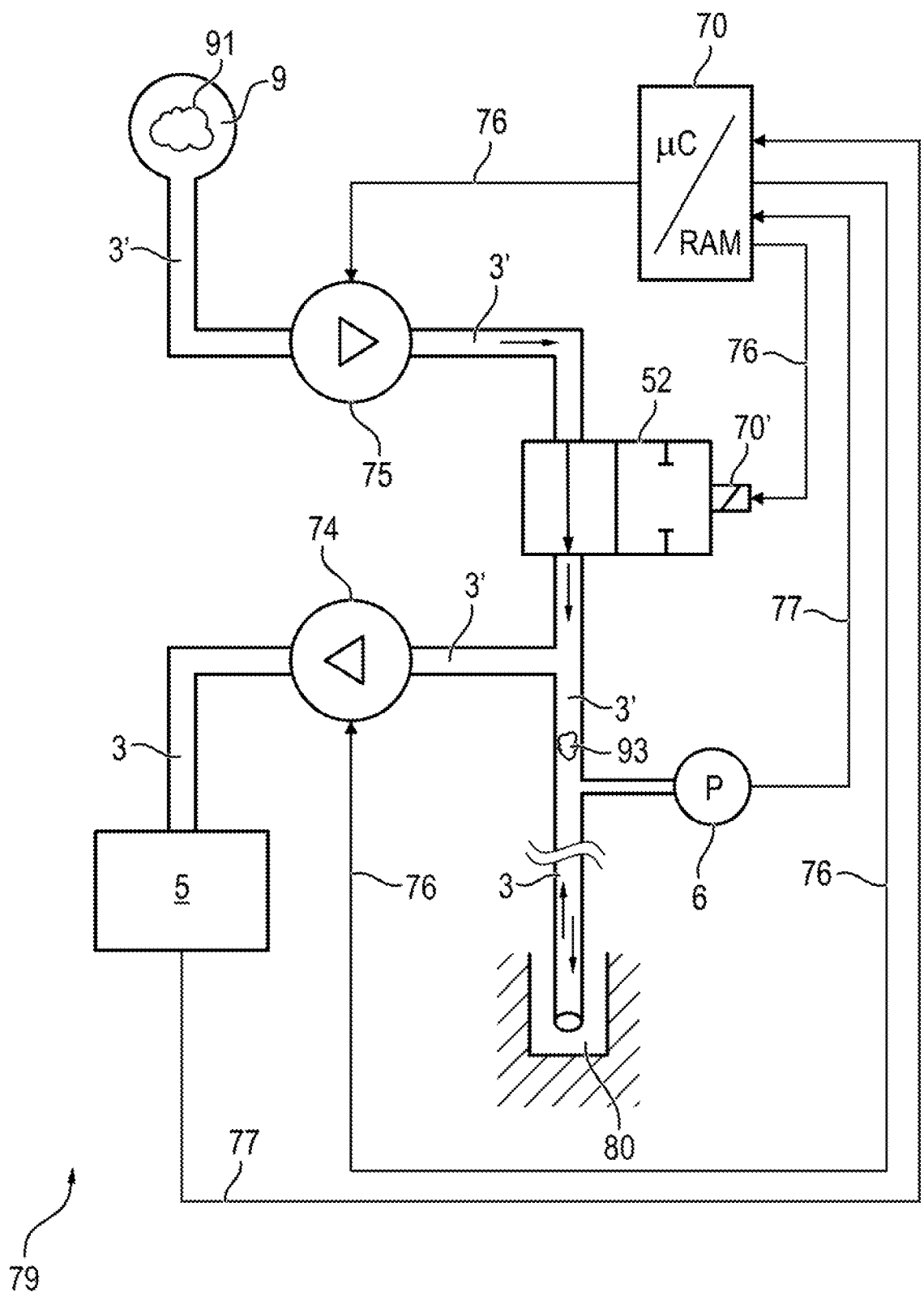
FIG. 3a is a schematic view of a fourth variant of the pumping device according to FIG. 1a in a first operating state.
Figure 3B:
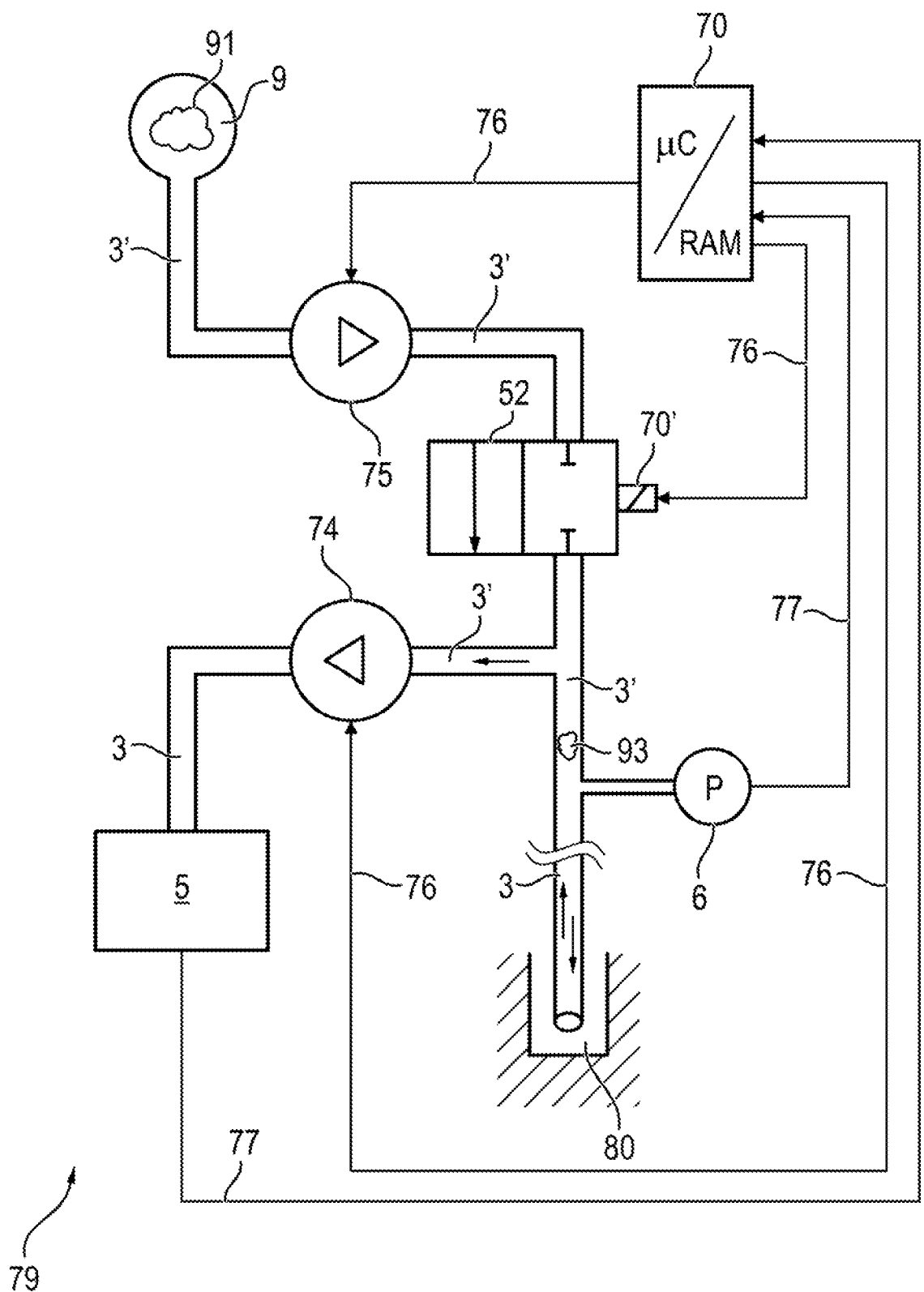
FIG. 3b is a schematic view of the fourth variant of the pumping device according to FIG. 1a in a second operating state.
Figure 4:
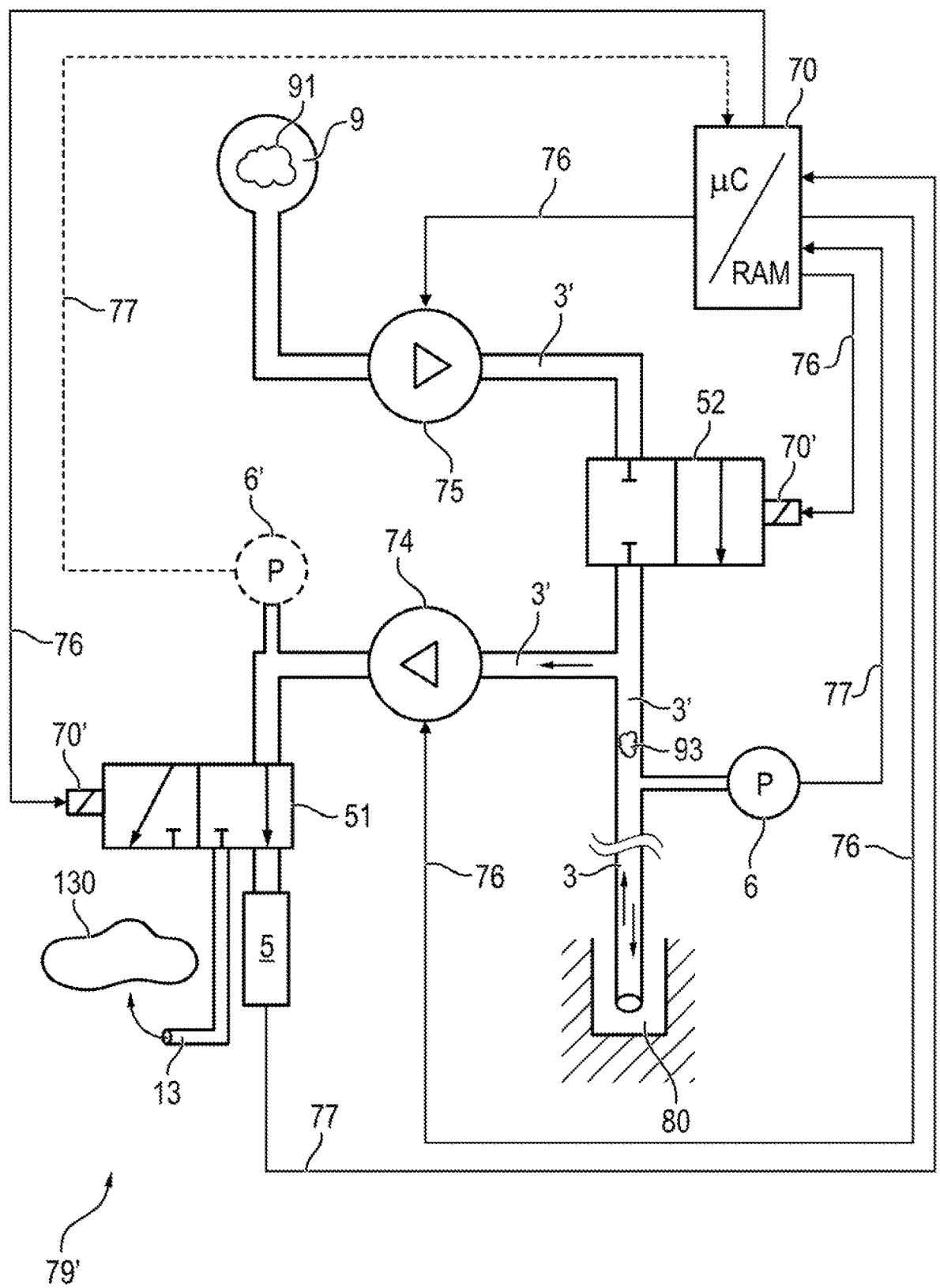
FIG. 4 is a schematic view of a variant of the testing device according to FIG. 3a and FIG. 3b with a gas outlet.

FIGS. 1b, 2a, 2b, 3a, 3b and 4 and the descriptions of FIGS. 1a, 2b, 2b, 3a, 3b and 4 describe additional embodiments of the pumping device with variants of pumps 74, 75 (FIGS. 1b, 2a, 2b, 3a, 3b and 4), arrangements of switching elements 70' (FIGS. 2a, 2b, 3a, 3b and 4) and pumps 74, 75 (FIGS. 2a, 2b, 3a, 3b and 4), configurations of arrays of valves 51, 52, 53 (FIGS. 1b, 2a, 2b, 3a, 3b and 4), in addition to other peculiar features of the configuration of the testing device 1 and of the pumping device 7, 7', 7", 7'", 79, 79' (FIGS. 1a, 1b, 2a, 2b, 3a, 3b and 4). The control, activation or control of components 51, 52, 53, 70', 71, 74, 75 (FIGS. 1a, 1b, 2a, 2b, 3a, 3b and 4) is carried out in these FIGS. 1a, 2a, 2b, 3a, 3b and 4 by the control unit 70 by means of control signals 76. The gas sensor 5 and the pressure sensor 6 for monitoring the pressure of the quantity of gas 93 flowing to the gas sensor 5, as well as the flow sensor 90 (FIG. 1c) provide measured values 77 to the control unit 70. An optional gas outlet 13, whose mode of action is described in more detail in FIG. 4 and in the description of FIG. 4, is indicated in this FIG. 1a.

The control unit 70 is configured to perform the testing of the operational capability of the gas guide element 3 on the basis of the measured values 77 of the pressure sensor 6. The control unit 70 is further configured optionally also to include measured values 77 of the pressure sensor 6 for the control of the pumping device 7, 7', 7", 7'", 79, 79' and the components 51, 52, 53, 70', 71, 74, 75 thereof (FIGS. 1a, 1b, 2a, 2b, 3a, 3b and 4) and to also include signals, such as parameters for controlling the pumping device 7 in the testing of the operational capability of the gas guide element 3. The control unit 70 is further configured to use measured values 77 of the gas sensor 5 for the analysis of gas concentrations at the remotely located measuring location 80.

A plurality of internal gas guide elements 3', which are necessary for the internal connections of the components 6, 71, 9, 9' (FIG. 1a) and 52, 53, 71, 74, 75, 9, 9' (FIGS. 1a, 1b, 2a, 2b, 3a, 3b and 4) within the pumping device 7, are provided in the pumping device 7. The separation of the gas guide elements 3 from the internal gas guide components 3' is not unambiguous, and all gas guide elements 3, 3' rather represent together the necessary fluidic connections between the gas sensor 5, the pressure sensor 6, the pumping device 7 and the components thereof and the remotely located measuring location 80. The testing of the operational capability of the gas guide elements 3, 3' also takes place together, because a reliable operating state of the gas-measuring system 11 can also only be ensured if all the fluidic connections necessary in the respective measuring application are in an error-free state. In addition to the test gas source 9, an optional scavenging gas source 9' for storing a scavenging gas 91', which is configured and intended for providing scavenging gas 91' for feeding the scavenging gas 91' to the remotely located measuring location 80 by means of the pumping device, is also arranged at the pumping device 7. This makes possible the scavenging of the pumping device 7 and of the gas guide elements 3, 3' with the scavenging gas 91', for example, to create defined gas states in the components 3, 3', 7, 5, 80, 6, 71 of the testing device 1 and of the gas-measuring system 11 as boundary conditions for the start of the testing of the operational capability of the gas guide element 3.

As was explained above, the control unit 70 is configured to receive measured values 77 detected and provided by the pressure sensor 6, which indicate a gas composition in the form of a specific density or dynamic viscosity, and to store the measured values 77 detected and provided by the pressure sensor 6, as well as the measured values 77 detected and provided by the gas sensor 5, in a memory 69, which is associated with the control unit 70 and is arranged in or at the control unit 70. The control unit 70 carries out the determination of the operational capability of the gas guide element 3 so as to coordinate an interaction of the pumping device 7 with the pressure sensor 6 by means of a sequence of steps.

Starting from a measuring operation, the control unit 70 puts the pumping device 7 into a first operating state 65 for a first predefined time period 81 in a first step 61, so that a quantity of test gas 91 is delivered from the test gas source 9 to the remotely located measuring location 80 by means of the gas guide element 3.

The duration of the first predefined time period 81 is configured by the control unit 70 on the basis of technical properties 33 of the gas guide element 3 and on the basis of technical properties 73 of the pumping device 7 such that the gas guide element 3 is filled with the test gas 91 over a length 34 from the remotely located measuring location 80 to the pumping device 7. The technical properties 73 of the pumping device 7 comprise essentially characteristics of the components 52, 53, 71, 74, 75, 9, 9' (FIGS. 1a, 1b, 2a, 2b, 3a, 3b and 4), such as flow rate and pressurized dispensing ranges, which the pumping device 7 provides for delivering the quantity 93 of test gas 91 from the test gas source 9 to the remotely located measuring location 80 by means of the gas guide element 3 in the first operating state 65. Furthermore, the technical properties 73 of the pumping device 7 also comprise the manner of arrangement of the gas source 9 at the pumping device 7, i.e., dimensions, such as the length 34 and the flow cross sedition of a section of the gas guide element 3, which section is arranged and intended therefor. The technical properties of the gas guide element 3 comprise here dimensions, such as an overall length from the pumping device 7, from the pressure sensor 6 and/or from the gas sensor 5 to the remotely located measuring location 80 and a line diameter belonging to the overall length of the gas guide element 3, so that a total gas volume present in the gas guide element 3 can be determined from this by the control unit 70. However, the technical properties 33 of the gas guide element 3 may also comprise the technical properties of individual parts of the gas guide element 3, i.e., flow cross sections and lengths 34 of different line sections of the gas guide element 3, in case of a multipart gas guide element 3. In addition, information on the material, wall thickness, geometric shape (round, elliptical, square), as well as information on a difference in level between the remotely located measuring location 80 and the pumping device 7, the pressure sensor 6 or the gas sensor 5 may also be comprised in the technical properties 33 of the gas guide element 3. Knowing the technical properties of the individual parts of the gas guide element 3, the control unit 70 is able to also determine the total gas volume of the multipart gas guide element 3.

In a second step 62, the control unit 70 puts the pumping device 7 into a second operating state 66 for a second predefined time period 82, so that a quantity of gas 93 is delivered from the remotely located measuring location 80 to the pressure sensor 6 or to the gas sensor 5 by means of the gas guide element 3. The duration of the second predefined time period 82 is configured by the control unit 70 on the basis of the first predefined time period 81 and on the basis of the technical properties 33 of the gas guide element 3 and on the basis of the technical properties 73 of the pumping device 7. The control unit 70 receives and detects a plurality of measured values 77 provided by the pressure sensor 6 during the second predefined time period 82. The control unit 70 stores in the memory 69 a then current measured value 72 of the measured values 77 provided by the pressure sensor 6 as a first comparison data value 78 in the second step 62 at the beginning of the second predefined time period 82 and a then current measured value 72' of the measured values 77 provided by the pressure sensor 6 as a second comparison data value 78' at the end of the second predefined time period 82.

In a third step 63, the control unit 70 performs a comparison between the first comparison data value 78 and the second comparison data value 78' and determines an indicator 86 of the operational capability of the gas guide element 3 on the basis of the comparison between the first comparison data value 78 and the second comparison data value 78' and of a predefined comparison criterion 85. The indicator of the operational capability of the gas guide element 3 can be put by the control unit 70 into the "capable of operating" state by means of the predefined comparison criterion 85 if it is found as a result of the comparison between the first comparison data value 78 and the second comparison data value 78' that the difference in the gas composition between the first comparison data value 78 and the second comparison data value 78' is lower than a predefined difference between the comparison data values 78, 78'. For example, a difference in a range of <3% to <5% shall be mentioned here. Depending on the configuration of the gas-measuring system 11 and the complexity of the arrangement of gas guide elements 3 and connection elements, a range of 0.01% to 10% may be practicable as a difference in the gas composition as a predefined comparison criterion 85 for the testing of the operational capability of the gas guide element 3. In case of a small difference between the comparison data values 78, 78', it is obtained as a result of the operational capability of the gas guide element 3 by the control unit 70 that the gas composition has not changed significantly in the gas guide element 3 over the entire length 34 from the remotely located measuring location 80 to the pressure sensor 6 or to the gas sensor 5 during the time period and no leak A 89 is consequently present in the gas guide element 3.

In a fourth step 64, the control unit 70 determines an output signal 88, which indicates the determined indicator 86 of the operational capability of the gas guide element 3 and provides this output signal 88.

This FIG. 1a shows an optional output and alarm generation unit 100. The output signal 88 is provided in this configuration with the output and alarm generation unit 100 by the control unit 70 to the output and alarm generation unit 100, so that it is now made possible to output a status on the basis of the determined indicator 86 of the operational capability of the gas guide element 3 or to generate an alarm in case of a leakage situation A 89. The output and alarm generation unit 100 usually has display elements, such as alphanumeric display lines or a graphics display for the output and usually acoustic signal generation elements, such as horns or other sound generators (loudspeakers) and optical alarm generation elements, for example, blinking lighting devices (incandescent lamps, LED) for the alarm generation. The output and alarm generation unit 100 may be arranged close by as a part of the gas-measuring system 11 or at another location, not shown in this FIG. 1a, and may be connected to the gas-measuring system 11, for example, as a module or assembly unit of an optional analysis system 101 in a data network.

Figure 1B:
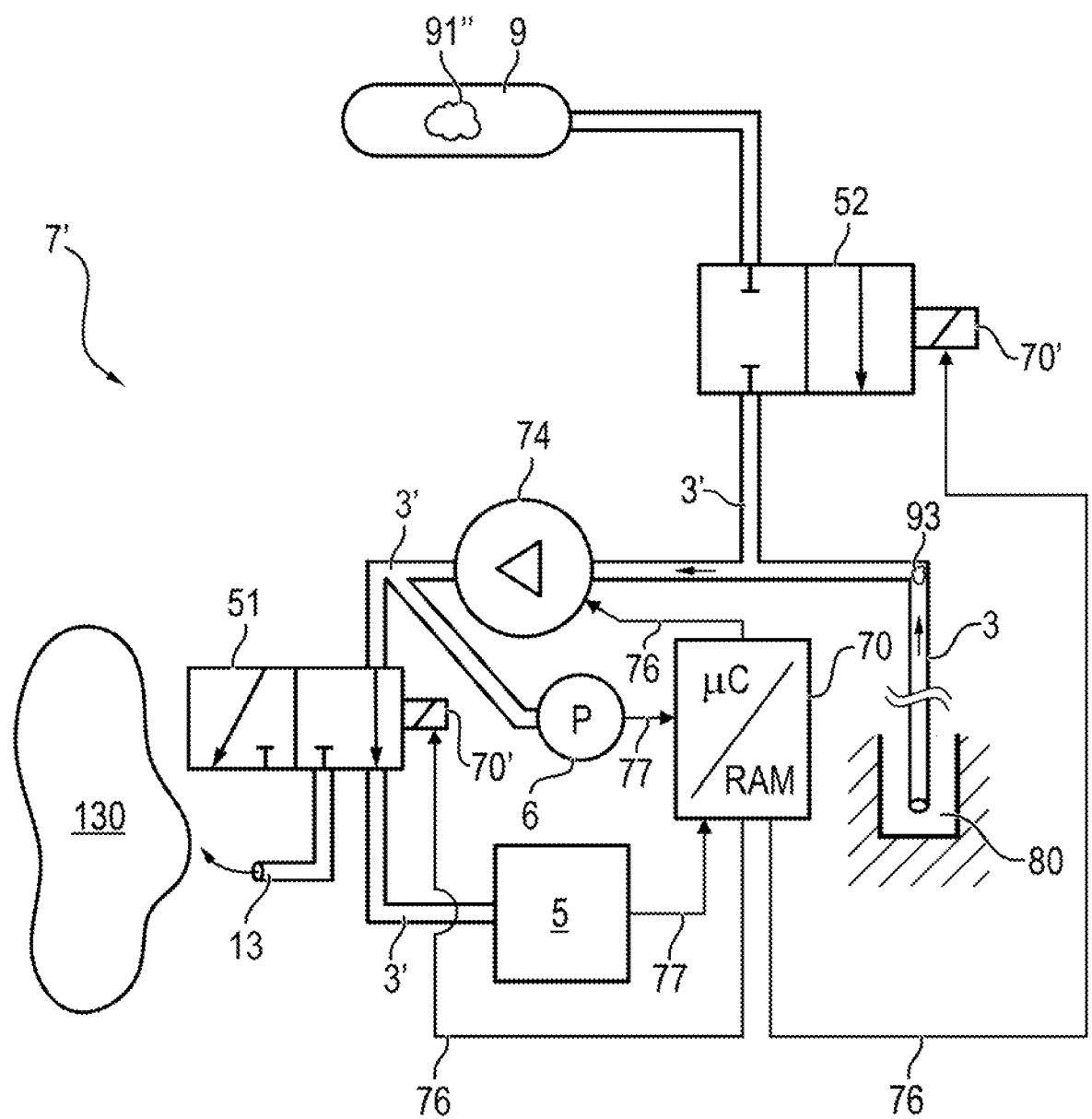

FIG. 1b shows a second variant 7' of the pumping device according to the testing device 1 shown in FIG. 1a. Identical components in FIGS. 1a, 1b are designated by the same reference numbers in FIGS. 1a, 1b. This variant of the pumping device 7' according to this FIG. 1b is based on the testing device 1 according to FIG. 1a with test gas source 9, control unit 70 and control signals 76, gas sensor 5, pressure sensor 6, the measured values 77, switching elements 70' and gas guide elements 3, 3' with fluidic connection to the located measuring location 80, gas outlet 13, and it additionally has a 2/2-way valve 52, a 3/2-way valve 51 and a unidirectionally delivering pump 74.

The test gas source 9 is configured in this FIG. 1b as a pressure tank, in which test gas 91" is stored in the liquid state under an admission pressure and is provided for delivery to the remotely located measuring location 80. The 2/2-way valve 52 is activated in the pumping device 7' by the control unit 70 in order to allow the test gas 91" to flow into the gas guide element 3. A pressure release takes place during the inflow, so that gaseous test gas will now flow into the gas guide element 3. Suitable test gases 91" for storage in the liquid state under pressure are, for example, propane, butane, and propane/butane mixtures.

The 2/2-way valve 52 can be used to avoid a state in which the test gas 91 can directly reach the gas sensor 5 from the test gas source 9 or is delivered by means of the pump 74. By means of a control signal 76, the control unit 70 can activate a switching element 70' on the valve 52 in order to open the valve 52, so that the test gas 91 can reach the internal gas guide element 3' for being fed to the pump 74 from the test gas source 9 only during the first operating state 65 (FIG. 1a).

A gas outlet 13, whose function and whose advantages are also described in more detail in FIG. 4 and in the description of FIG. 4, is arranged in the pumping device 7' in this FIG. 1b. Just like the gas sensor 5, the gas outlet 13 is connected to the pump 74 in this FIG. 1b by means of the 3/2-way valve 51. The 3/2-way valve 51 can be put by the control unit 70 into two different states of flow. This makes possible the delivery of the quantity of gas 93, which is delivered by means of the pump 74 from the remotely located measuring location 80, to the gas sensor 5 or through the gas outlet 13 into the surrounding area 130 by means of a gas discharge line.

The pressure sensor 6 is shown in this FIG. 1b as a part of the pumping device 7', and it is configured to detect measured values of a pressure of gas in the gas guide element 3 and to transmit pressure signals 77 to the control unit 70. By means of the measured pressured values of the pressure signals 77, the control unit 70 is able to control the pump 74 in terms of the delivery pressure and/or the flow rate. For example, a pump motor driving the pump 74 can be controlled or regulated for this by means of characteristics $[P=F(n), n=F(U)]$ for the pressure P in terms of a speed of rotation n corresponding to the control signal U 76, configured as a current, voltage or PWM signal, with inclusion of the measured value of the pressure signal 77 of the pressure. The control of the pump is working with characteristic curves which incorporate dependencies between pressure P and revolution n, where P is a function of n and n is depending from a control signal U (74), provided by the control unit (70) to the pump (70). The control signal U is representing an electrical signal, like a DC- or AC-Voltage (U[V]) or current DC- or AC-Current (I[A]), or a pulse width modulated (Voltage) signal (PWM).

FIGS. 2a and 2b show a third variant 7''' of the pumping device according to the testing device 1 shown in FIG. 1a in a first operating state (FIG. 2a) and in a second operating state (FIG. 2b). FIGS. 2a and 2b are explained in a joint description. Identical components in FIGS. 1a, 2a and 2b are designated by the same reference numbers in FIGS. 1a, 2a, 2b. The first operating state corresponds to the first operating state 65 according to FIG. 1a and it makes it possible to deliver test gas 91 from the test gas source 9 to the remotely located measuring location 80. The second operating state corresponds to the second operating state 66 according to FIG. 1a and it makes possible a return delivery from the remotely located measuring location 80 to the pumping device 7' and to the gas sensor 5. The pumping device 7''' has a unidirectionally delivering pump 74, which is connected to an array of two so-called 3/2-way valves 51, 53 by means of internal gas guide elements 3'.

The 3/2-way valves 51, 53 can be put by the control unit 70 into two different states of flow. These states of flow of the 3/2-way valves 51, 53 can be set by the control unit 70 by means of control signals 76 and switching elements 70' belonging to the valves 51, 53, so that the direction of delivery of the pumping device 7''' is reversible, i.e., a gas quantity 93 of test gas 91 delivered from the test gas source 9 to the remotely located measuring location 80 in the first operating state (FIG. 2a), or the quantity of gas 93 with the test gas 91 is delivered from the remotely located measuring location 80 back to the pumping device 7''' and to the gas sensor 5. To avoid a state in which test gas 91 can directly reach the gas sensor 5 from the test gas source 9 or is delivered by means of the pump 74, a 2/2-way valve 52 is arranged at the test gas source. The control unit 70 can activate a switching element 70' on the valve 52 by means of a control signal 76 in order to open the valve 52, so that test gas 91 can enter the internal gas guide element 3' for being fed to the valves 51, 53. The control unit 70 configures the two operating states 65 (FIG. 1a, FIG. 2a) and 66 (FIG. 1a, FIG. 2b) by means of controlling the switching elements 70' on the valves 51, 52 by means of the control signals 76 as they arise from the differences in the valve positions shown in FIGS. 2a and 2b. Measured values 77 detected by the gas sensor 5 are analyzed by the control unit 70 for performing the testing of the operational capability of the gas guide element 3, as was described above in connection with FIG. 1a.

A fourth variant 79 of the pumping device according to the testing device 1 shown in FIG. 1a is shown in FIGS. 3a and 3b in a first operating state (FIG. 3a) and in a second operating state (FIG. 3b). FIGS. 3a and 3b are explained in a joint description of the figures. Identical components in FIGS. 1a, 3a, 3b are designated by the same reference numbers in FIGS. 1a, 3a, 3b. The first operating state corresponds to the first operating state 65 according to FIG. 1a and it makes possible the delivery of test gas 91 from the test gas source 9 by means of the gas guide element 3 to the remotely located measuring location 80. The second operating state corresponds to the second operating state 66 according to FIG. 1a and it makes possible a return delivery from the remotely located measuring location 80 back to the pumping device 79 and to the gas sensor 5. The pumping device 79 has an array of two unidirectionally delivering pumps 74, 75 in an antiparallel arrangement, which are connected by means of internal gas guide elements 3'. The two pumps 74, 75 can be activated separately by means of control signals 76, so that two directions of delivery can be obtained with the pumping device 79, depending on activation of the pumps 74. 75. The quantity of gas 93 of test gas 91 is delivered in the first operating state (FIG. 3a) from the test gas source 9 to the remotely located measuring location 80. In the second operating state (FIG. 3b), this quantity of gas 93 of test gas 91 is delivered from the remotely located measuring location 80 back to the pumping device 79 and to the gas sensor 5. To avoid a state in which the test gas 91 can directly reach the gas sensor 5 from the test gas source 9 or is delivered by means of the pump 74, a 2/2-way valve 52 is arranged at the test gas source. The control unit 70 can activate a switching element 70' on the valve 52 by means of a control signal 76 in order to open the valve 52, so that test gas 91 can enter from the test gas source 9 the internal gas guide element 3' for being fed to the two pumps 74, 75. To set the first operating state 65 (FIG. 1a, FIG. 3a), the control unit 70 activates the second pump 75 by means of the control signals 76 and opens the valve 52. The second pump 75 delivers the test gas 91 into the gas guide element 3 to the remotely located measuring location 80. The first pump 74 is deactivated in the first operating state 65 (FIG. 1a, FIG. 3a) and it does not deliver any quantities of gas. To set the second operating state 66 (FIG. 1a, FIG. 3b), the control unit 70 activates the first pump 74 and closes the valve 52 by means of the control signals 76. The first pump 75 delivers the test gas 91 from the remotely located measuring location 80 back to the gas sensor 5. The second pump 75 is deactivated in the second operating state 66 (FIG. 1a, FIG. 3b) and it does not deliver any quantities of gas. Measured values 77 detected by the gas sensor are analyzed by the control unit 70 for performing the testing of the operational capability of the gas guide element 3, as was described in connection with FIG. 1a above.

FIGS. 2a and 2b, 3a and 3b show a pressure sensor 6 as a respective part of the pumping device 79, which is configured to detect measured values of a pressure 77 at the gas guide element 3 and to transmit them to the control unit 70. By means of the measured values of the pressure 77, the control unit 70 is able to activate the pump 74 (FIGS. 2a, 2b) or the pumps 74, 75 (FIGS. 3a, 3b) and to control them in terms of the delivery pressure and/or the flow rate. The pump may be controlled in different ways, as is explained in the description of FIG. 1b. Furthermore, the control unit 70 is able to carry out the testing of the operational capability of the gas guide element 3 by means of the measured values of the pressure 77.

FIG. 4 shows a variant 79' of the testing device according to FIG. 3b with a gas outlet 13. The variant of the pumping device 79' is based on the configurations shown and described in connection with FIGS. 3a and 3b with two pumps 74, 75 arranged in an antiparallel arrangement, test gas source 9, control unit 70 and control signals 76, 2/2-way valve 52, gas sensor 5, pressure sensor 6, measured values 77, switching elements 70' and gas guide elements 3, 3' with fluidic connection to the remotely located measuring location 80. Identical components in FIGS. 1a, 3a, 3b, 4 are designated by the same reference numbers in FIGS. 1a, 3a, 3b, 4. The gas outlet 13 and the gas sensor 5 are connected fluidically to the first pump 74 by means of a 3/2-way valve 51. The 3/2-way valve 51 can be set for this by the control unit 70 into two different states of flow by means of a control signal 76. This makes it possible in the state of flow of the valve as shown in FIG. 4 either to feed the quantity of gas 93, which is delivered by means of the activated first pump 74 from the remotely located measuring location 80, to the gas sensor 5, or to send it through the gas outlet 13 into a surrounding area 130 by means of a gas discharge line.

Another pressure sensor 6' is arranged in this FIG. 4 at the inlet of the valve 51 and at the outlet of the pump 74, and the measured value 77 of this pressure sensor 6' is provided to the control unit 70, so that the control unit 70 is able to use both measured values 77 in the gas guide element 3, which connects the pumping device 7 with the remotely located measuring location 80 by means of the pressure sensor 6, and pressure measured values by means of the pressure sensor 6' at the internal gas guide element 3', which connects the pumping device 7 to the gas sensor 5, to control the pump 74 and the valves 51, 52 during the performance of the testing of the operational capability of the gas guide element 3.

The configuration shown in FIG. 4 makes possible the switchover of the quantity of gas 93 delivered from the remotely located measuring location 80 into the gas outlet 13 or to the gas sensor 5. The possibility of switchover of the quantity of gas 93 delivered from the remotely located measuring location 80 into the gas outlet 13 offers the advantage that the gas sensor 5 can be uncoupled from scavenging gas, measured gas or test gas by means of the control signal 76 by the control unit 70 at any time during the testing of the operational capability of the gas guide element 3, so that, for example, a testing, resetting, adjustment (offset, characteristic) or calibration of the gas sensor 5 can be performed or prompted by the control unit 70 even during the ongoing testing of the operational capability of the gas guide element 3. Furthermore, the arrangement of the gas outlet 13 with the associated 3/2-way valve 51 offers the advantage that scavenging of the gas-measuring system 11 (FIG. 1a), of the pumping device 79' as well as of the gas guide element 3 can be carried out, as is described in connection with FIG. 1a, with the scavenging gas 91' (FIG. 1a) by means of a scavenging gas 91' (FIG. 1a) from a scavenging gas source 9' (FIG. 1a) without the scavenging gas 91' (FIG. 1a) having to be fed to the gas sensor. This leads to the advantage that there are no waiting times or recovery times of the gas sensor 5 for detecting the measured gas by the gas sensor 5 in the course of the further operation after the scavenging of the gas guide element 3.

While specific embodiments of the invention have been shown and described in detail to illustrate the application of the principles of the invention, it will be understood that the invention may be embodied otherwise without departing from such principles.

APPENDIX

List of Reference Numbers

1 Testing device
3 Gas guide element (hose line)
3' Internal gas guide elements in the pumping device 7
5 Gas sensor
6, 6' Pressure sensor
7, 7', 7''', 79, 79' Pumping device
9 Test gas source, test gas tank, gas generator
9' Scavenging gas source
11 Gas-measuring system
13 Gas outlet
33 Technical properties of the gas guide element
34 Length of the gas guide element to the measuring location
51 First 3/2-way valve 52 2/2-way valve
53 Second 3/2-way valve
61, 62, 63, 64 Steps of the sequence of steps
65 First operating state
66 Second operating state
67 Additional operating state
69 Memory
70 Control unit
70' Switching elements
71 Bidirectionally delivering pump
70' Switching elements
72 Current measured value at the beginning of the second operating state
72' Current measured value at the end of the second operating state
73 Technical properties of the pumping device
74 First pump (unidirectional)
75 Second pump (unidirectional)
76 Control signals, activating signals, switching signals
77 Measured values, set of measured values
78 First comparison data value
78' Second comparison data value
80 Remotely located measuring location
81 First predefined time period
82 Second predefined time period
85 Comparison criterion
86 Indicator of the operational capability
88 Output signal
89, 89' Leak A
90 Flow sensor
91 Quantity of test gas
91' Quantity of scavenging gas
91" Test gas stored in the liquid stale
93 Quantity of gas
100 Output and alarm generation unit
101 Analysis system in the data network
130 Surrounding area

What is claimed is:

1. A testing device for determining an operational capability of a gas guide element of a gas-measuring system, which gas guide element is configured to route or guide a fluid, and which gas-measuring system comprising a gas sensor system with at least one gas sensor, a pumping device comprising a pump configured to deliver gas, a state of flow sensor sensing either a state of flow in the gas guide element or an operating state of the pumping device, and the gas guide element, the testing device comprising:
   a test gas source; and
   a control unit with an associated memory and operative connections to the pumping device, the sensor system and the state of flow sensor, wherein:
   the gas guide element is arranged between the pump, the state of flow sensor and the gas sensor system;
   the gas guide element, the gas sensor system and the pumping device being connected to one another fluidically and configured for interaction such that a quantity of gas can be fed to the gas sensor system and to the state of flow sensor, from a measuring location located remotely from the gas sensor, and such that a quantity of gas can be fed to the remotely located measuring location by the pumping device;
   the state of flow sensor is configured to detect a measured value, which indicates a pressure in the gas guide element;
   the test gas source is arranged at the pumping device and the gas guide element;
   the gas sensor system and the pumping device are connected fluidically such that a quantity of test gas can be fed as a quantity of gas to the remotely located measuring location from the test gas source;
   the control unit is configured to receive measured values detected and provided by the state of flow sensor, which measured values indicate the state of flow in the gas guide element or an operating state of the pumping device;
   the control unit is configured with the associated memory to store the measured values detected and provided by the state of flow sensor, which indicates the state of flow in the gas guide element or an operating state of the pumping device;
   the control unit is configured, to determine the operational capability of the gas guide element, to coordinate the pumping device in interaction with the state of flow sensor by means of a sequence of steps beginning from a measuring operation, the sequence of steps comprising:
   the control unit putting the pumping device into a first operating state for a first predefined time period, so that a quantity of test gas is delivered from the test gas source to the gas guide element in a direction toward the remotely located measuring location by means of the gas guide element and selecting a duration of the first predefined time period based on technical properties of the gas guide element and based on technical properties of the pumping device such that the gas guide element is filled with the test gas over a length from the remotely located measuring location to the pumping device;
   the control unit putting the pumping device into a second operating state for a second predefined time period in a second step, so that a quantity of gas is delivered by means of the gas guide element from the gas guide element in a direction from the remotely located measuring location, to the state of flow sensor and a duration of the second predefined time period is selected by the control unit based on the first predefined time period and based on technological properties of the pumping device;
   the control unit receiving, during the second predefined time period, a plurality of measured values provided by the state of flow sensor, which indicate the state of flow in the gas guide element or an operating state of the pumping device, and the control unit determining, in the second step, at a beginning of the second predefined time period, a beginning value of the system size, which value represents a current density and/or dynamic viscosity of the gas in the gas guide element, and stores the beginning value of the system size as a first comparison data value in the memory, and at the end of the second predefined time period, the control unit determines an end value of the system size, which represents the current density and/or dynamic viscosity of the gas in the gas guide element, and stores the end value as a second comparison data value in the memory;
   the control unit performing a comparison between the first comparison data value and the second comparison data value and determines an indicator of the operational capability of the gas guide element based on the comparison between the first comparison data value and the second comparison data value and a predefined comparison criterion; and the control unit determining an output signal which indicates the indicator of the operational capability of the gas guide element and the control unit providing the output signal as an output.

2. A testing device in accordance with claim 1, wherein measured values detected and provided by the state of flow sensor, which indicate the state of flow in the gas guide element or an operating state of the pumping device, are used by the control unit as values of the system size, which represent differences in the density and/or in the dynamic viscosity of the test gas.

3. A testing device in accordance with claim 1, wherein:
measured values detected and provided by the state of flow sensor, which indicate the state of flow in the gas guide element or an operating state of the pumping device, are used by the control unit as values of the system size, which represent differences in the density and/or in the dynamic viscosity of the test gas; and
the state of flow sensor, which indicates the state of flow in the gas guide element or an operating state of the pumping device, is configured as a pressure sensor.

4. A testing device in accordance with claim 1, wherein measured values detected and provided by the state of flow sensor, which indicate the state of flow in the gas guide element or an operating state of the pumping device, are used by the control unit as values of the system size, which represent differences in the density and/or in the dynamic viscosity of the test gas, wherein the state of flow sensor, which indicates the state of flow in the gas guide element or an operating state of the pumping device, is configured as a flow sensor.

5. A testing device in accordance with claim 1, wherein parameters, which indicate operating states of the pump arranged in or at the pumping device, are used by the control unit as values of the system size, which represent differences in the density and/or in the dynamic viscosity of the test gas.

6. A testing device for determining the operational capability of a gas guide element of a gas-measuring system, which gas guide element is configured to route or guide a fluid, and which gas-measuring system comprises a gas sensor system with at least one gas sensor, a pressure sensor, a pumping device, and the gas guide element, the testing device comprising:
a test gas source; and
a control unit with an associated memory and operative connections to the pumping device, the gas sensor system and the pressure sensor, wherein:
the gas guide element is arranged between the pump, the pressure sensor and the gas sensor system;
the gas guide element, the gas sensor system, the pressure sensor and the pumping device are connected fluidically to one another and are configured for interaction such that a quantity of gas can be fed to the gas sensor system and to the pressure sensor from the gas guide element in a direction from a measuring location located remotely from the gas sensor and a quantity of gas can be fed to the gas guide element in a direction toward the remotely located measuring location by the pumping device;
the pressure sensor is configured to detect a measured value, which indicates a pressure in the gas guide element;
the test gas source is arranged at the pumping device and the gas guide element;
the gas sensor system and the pumping device are connected fluidically such that a quantity of test gas can be fed to the gas guide element in the direction toward the remotely located measuring location as a quantity of gas from the test gas source;
the control unit is configured to receive measured values detected and provided by the pressure sensor;
the control unit is configured with the associated memory to store the measured values detected and provided by the pressure sensor;
the control unit is configured to determine the operational capability of the gas guide element and to coordinate the pumping device in interaction with the pressure sensor by means of a sequence of steps beginning from a measuring operation, the sequence of steps comprising:
the control unit putting the pumping device into a first operating state for a first predefined time period so that a quantity of test gas is delivered from the test gas source to the gas guide element in the direction toward the remotely located measuring location by means of the gas guide element and selecting a duration of the first predefined time period by the control unit based on technical properties of the gas guide element and based on technical properties of the pumping device such that the gas guide element is filled with the test gas over a length from the remotely located measuring location to the pumping device;
the control unit putting the pumping device into a second operating state for a second predefined time period, so that a quantity of gas is delivered from the remotely located measuring location to the pressure sensor and to the gas-measuring system by means of the gas guide element and selecting a duration of the second predefined time period based on the first predefined time period and based on technical properties of the gas guide element and based on technical properties of the pumping device;
the control unit receiving a plurality of measured values provided by the pressure sensor during the second predefined time period at a beginning of the second predefined time period and storing a beginning current measured value of the provided measured values as a first comparison data value in the memory and at an end of the predefined time period storing an end current measured value of the provided measured values as a second comparison data value in the memory;
the control unit performing a comparison between the first comparison data value and the second comparison data value and determining an indicator of the operational capability of the gas guide element based on the comparison between the first comparison data value and the second comparison data value and a predefined comparison criterion; and
the control unit determining an output signal, which indicates the indicator of the operational capability of the gas guide element and the control unit providing the output signal as an output.

7. A testing device in accordance with claim 6, further comprising a scavenging gas source arranged at the pumping device, wherein:
the scavenging gas source, arranged at the pumping device, the gas guide element, the gas sensor system and the pumping device are fluidically connected to one another such that a quantity of scavenging gas can be fed to the gas sensor system from the scavenging gas source;
the control unit is configured to put the pumping device into an expanded operating state, so that a quantity of scavenging gas is delivered by to the gas guide element in the direction toward the remotely located measuring location from the scavenging gas source; and the quantity corresponds to a quantity to completely fill the gas guide element with the scavenging gas over the length from the remotely located measuring location to the pumping device.

8. A testing device in accordance with claim 6, wherein the test gas source and/or the scavenging gas source are embodied as a configuration of a container with an array of valves, switching devices or piezo dispensing elements and the valves, switching devices or piezo dispensing elements can be activated by the control unit by means of control signals such that the test gas and/or the scavenging gas are provided, sent or fed to the pumping device.

9. A testing device in accordance with claim 6, wherein:
the pumping device comprises a bidirectionally delivering pump with a direction of delivery that can be reversed by the control unit by means of a control signal such that either a quantity of measured gas is delivered from the gas guide element, in the direction from the remotely located measuring location, to the pumping device and to the gas sensor system, or a quantity of test gas is delivered from the test gas source to the gas guide element in the direction of the remotely located measuring location; and
the bidirectionally delivering pump is arranged in the pumping device.

10. A testing device in accordance with claim 6, wherein:
the pumping device is configured as an array of two 3/2-way valves; and
the control unit sets respective states of flow of the 3/2-way valves by means of control signals such that either a quantity of measured gas is delivered from the gas guide element in the direction from the remotely located measuring location to the pumping device and to the gas sensor system, or a quantity of test gas is delivered from the test gas source to the remotely located measuring location.

11. A testing device in accordance with claim 6, wherein:
the pumping device is configured as an array of two pumps arranged in an antiparallel arrangement; and
the control unit activates by means of a control signal either one pump or another pump of the array of two pumps so that either a quantity of measured gas is delivered from the gas guide element in the direction from the remotely located measuring location to the pumping device and to the gas sensor system, or a quantity of test gas is delivered from the gas guide element in the direction from the test gas source to the remotely located measuring location.

12. A testing device in accordance with claim 6, further comprising a gas outlet arranged in the testing device and a 3/2-way valve arranged in the pumping device, wherein a state of flow of the 3/2-way valve is set by the control unit by means of a control signal such that delivery of the quantity of gas from the gas guide element in the direction from the remotely located measuring location to the gas sensor system or delivery of the quantity of gas from the gas guide element in the direction from the remotely located measuring location into the gas outlet is ensured.

13. A testing device in accordance with claim 7, wherein:
a 2/2-way valve is provided with a state controlled by the control unit by means of a control signal such that the test gas or the scavenging gas is delivered as a quantity of gas to the gas guide element in the direction of the remotely located measuring location and no test gas or scavenging gas is delivered or can reach the gas sensor system directly from the test gas source; and
the scavenging gas source or the pumping device is arranged in or at the pumping device, the test gas source or the scavenging gas source.

14. A testing device in accordance with claim 6, wherein the test gas source is configured as a gas generator, which is activated by the control unit by means of a control signal and is configured to generate the test gas electrolytically, chemically or electrochemically.

15. A testing device in accordance with claim 6, wherein:
the test gas source is configured as a pressure tank with a shut-off valve;
the test gas is stored in the pressure tank under admission pressure in the liquid form and is provided for the pumping device for delivery to the gas guide element in the direction of the remotely located measuring location; and
the shut-off valve is controlled by the control unit by means of a control signal such that an inflow from the pressure tank to the remotely located measuring location is brought about and made possible.

16. A testing device in accordance with claim 1, wherein the state of flow sensor, which indicates the state of flow in the gas guide element or an operating state of the pumping device, is used by the control unit to control, by means of a control signal, the pumping device in terms of the delivery rate and/or the flow rate based on the measured values of the state of flow sensor.

17. A testing device in accordance with claim 1, wherein the pressure sensor and/or the flow sensor and/or a speed of rotation sensor are used by the control unit to control, by means of a control signal, the pumping device in terms of the delivery rate and/or the flow rate based on the measured values of the flow sensor and/or of the measured values of the speed of rotation sensor.

* * * * *